(12) United States Patent
Manam et al.

(10) Patent No.: US 7,250,438 B2
(45) Date of Patent: Jul. 31, 2007

(54) ANTI-BACTERIAL AND ANTI-CANCER SPIRO BETA-LACTONE/GAMMA-LACTAMS

(75) Inventors: Rama Rao Manam, San Diego, CA (US); Barbara C. Potts, Escondido, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 76 days.

(21) Appl. No.: 11/146,613

(22) Filed: Jun. 6, 2005

(65) Prior Publication Data

US 2006/0004079 A1 Jan. 5, 2006

Related U.S. Application Data

(60) Provisional application No. 60/592,909, filed on Jul. 29, 2004, provisional application No. 60/578,468, filed on Jun. 8, 2004.

(51) Int. Cl.
*A61K 31/407* (2006.01)
*C07D 491/107* (2006.01)

(52) U.S. Cl. ...................... 514/409; 548/410

(58) Field of Classification Search ................ 548/410
See application file for complete search history.

(56) References Cited

FOREIGN PATENT DOCUMENTS

JP 61172881 A 8/1986

OTHER PUBLICATIONS

Moloney et al., "The Oxazolomycins: A Structurally Novel Class of Bioactive Compounds," *Current Drug Discovery Technologies*, 2004, 1, 181-199.*
Mori, et al., "Structure of Oxazolomycin, a Novel β-Lactone Antibiotic", *Tetrahedron Lett.*, 1985, 26:1073-1076.
Ryu, et al., "16-Methyloxazolomycin, a New Antimicrobial and Cytotoxic Substance Produced by a *Streptomyces* sp.", *J. Antibiotics*, 1997, 50:1064-1066.
Ikeda, et al., "New Triene-β-Lactone Antibiotics, Triedimycins A and B", *J. Antibiotics*, 1991, 44:453-455.
Aizawa, et al., "Resistaphylin, a New Antibiotic. I", *J. Antibiotics*, 1971, 24-393-.
Ogura, et al., "Structure of a New Antibiotic Currromycin A Produced by a genetically modified strain of *Streptomyces hygroscopicus*, a polyether antibiotic producing organism", *J. Antibiotics*, 1985, 38:669-.
Gräfe, et al., "Biogenetic Studies on Oxazolomycin, a Metabolite of *Streptomyces albus* (Strain JA 3453)", *Liebigs Ann. Chem.*, 1992, 429-.
Ryu, et al., "Absolute Stereochemistry Determination of 16-Methyloxazolomycin Produced by a *Streptomyces* sp.", *J. Antibiotics*, 1999, 52:193-.
Kanzaki, et al., "Novel Bioactive Oxazolomycin Isomers Produced by *Streptomyces albus* JA3453", *Biosci. Biotechnol. Biochem.*, 1998, 62:438-.
Otani, et al., "Novel Triene-β-lactone Antibiotics, Oxazolomycin Derivative and Its Isomer, Produced by *Streptomyces* sp. KSM-2690", *J. Antibiotics*, 2000, 53:1397-.
Takahashi, et al., "Structure of Neooxazolomycin, an Antitumor Antibiotic", *Tett. Lett.*, 1985, 26:1077-.
Bulger et al., "A multicomponent coupling strategy of the triene component of the oxazolomycin antibiotics," *Organic & Biomolecular Chem.*, 1(21), 3726-3737, 2003.
International Search Report and Written Opinion for Application No. PCT/US2005/020131, mailed Dec. 16, 2005.

* cited by examiner

*Primary Examiner*—Kamal A. Saeed
*Assistant Examiner*—Andrew B. Freistein
(74) *Attorney, Agent, or Firm*—Knobbe, Martens, Olson & Bear, LLP

(57) ABSTRACT

Disclosed herein are novel spiro beta-lactone/gamma lactams for use in treating bacterial infections and cancer. The compounds are characterized by a terminal electron-withdrawing group such as a nitro group. Screening data shows antimicrobial activity against various bacterial cell lines, particularly gram-positive bacteria, and anti-cancer activity.

36 Claims, 12 Drawing Sheets

ANTI-BACTERIAL AND ANTI-CANCER SPIRO BETA-LACTONE/GAMMA-LACTAMS

RELATED APPLICATIONS

This application claims priority to U.S. Provisional Application No. 60/578,468 filed Jun. 8, 2004 and U.S. Provisional Application No. 60/592,909, filed Jul. 29, 2004, both of which are incorporated herein by reference.

BACKGROUND OF THE INVENTION

1. Field of the Invention

The present invention relates to compounds and methods for obtaining such compounds in the fields of chemistry and medicine. More specifically, the present invention relates to compounds and procedures for making compounds useful in the treatment of cancer and the treatment of bacterial infections.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused for example by bacteria are becoming increasingly difficult to treat and cure. For example, more and more bacteria are developing resistance to current antibiotics and chemotherapeutic agents. Examples of such bacteria include both gram positive and gram negative bacteria, including *Staphylococcus, Streptococcus, Mycobacterium, Enterococcus, Corynebacterium, Borrelia, Bacillus, Chlamidia, Mycoplasma*, and the like.

Therefore, a need exists for additional chemotherapeutics and antimicrobial agents to treat cancer and infectious disease. A continuing effort is being made by individual investigators, academia and companies to identify new, potentially useful chemotherapeutic and antimicrobial agents.

Marine-derived natural products are a rich source of potential new anti-cancer agents and antimicrobial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns.

SUMMARY OF THE INVENTION

In one embodiment, the invention provides compounds, pharmaceutical compositions, methods of producing compounds, and methods of treating cancer and microbial infections by administering compounds and compositions, wherein the compounds are represented by Formula (I):

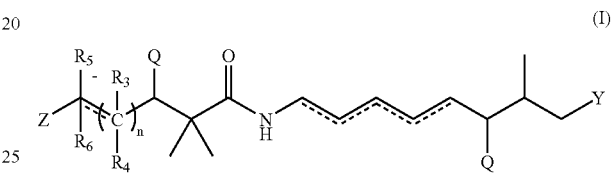

(I)

In the compound of Formula (I), $R_3$, $R_4$, $R_5$, and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, or may be absent when necessary to accommodate double bonds. Y has the following structure:

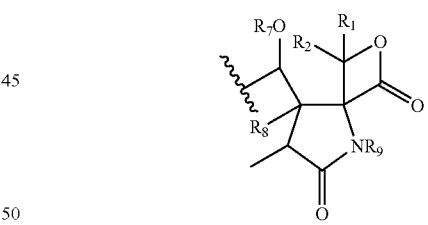

where $R_1$, $R_2$, and $R_8$ may each be separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

Any suitable electron withdrawing group can be selected for Z. For example, Z can be selected from the group consisting of optionally substituted heteroatom, $CX_3$, $CHX_2$, $CH_2X$, CN, C(O)X, C(O)O$R_{10}$, C(O)$R_{10}$, X, as defined herein, and optionally substituted aryl or heteroaryl including optionally substituted variants of the following residues: pyridine, pyrrole, furan, thiophene, imidazole, oxazole, and thiazole. In some embodiments, when Z is an optionally substituted heteroatom, it is selected from the group consisting of $NO_2$, $SO_3H$, and $OR_{11}$ where $R_{11}$ is selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl. In the compound of Formula (I), n can be 0, 1, 2, 3, 4, 5, 6, 7, 8, 9, or 10. In some embodiments n is less than 8. In one embodiment n is 7. When Z is an optionally substituted variant of oxazole, then n is preferably not 6.

Each X may be separately selected from the group consisting of F, Cl, Br, and I.

$R_{10}$ may be selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Each bond represented by a dashed and solid line in the structure of Formula (I) may either be a carbon-carbon single bond or a carbon-carbon double bond and if a carbon-carbon double bond, may have either cis or trans configuration. Where n is greater than 1, it is to be understood that each unit n is bonded to any adjacent units n via carbon-carbon single bonds or carbon-carbon double bonds with either cis or trans configuration.

In another embodiment, the invention provides compounds, pharmaceutical compositions, methods of producing compounds, and methods of treating cancer and microbial infections by administering compounds and compositions, wherein the compounds are represented by Formula (II):

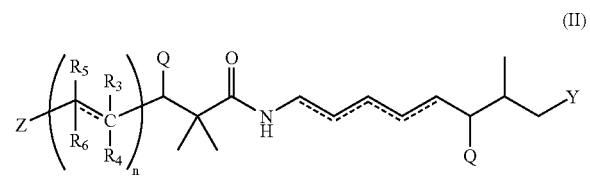

(II)

In the compound of Formula (II), $R_3$, $R_4$, $R_5$, and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, or absent when necessary to accommodate double bonds. Y has the following structure:

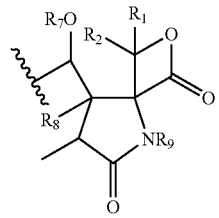

where $R_1$, $R_2$, and $R_8$ may each be separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

Any suitable electron withdrawing group can be selected for Z. For example, Z can be selected from the group consisting of optionally substituted heteroatom, $CX_3$, $CHX_2$, $CH_2X$, CN, C(O)X, C(O)O$R_{10}$, C(O)$R_{10}$, X, as defined herein, and optionally substituted aryl or heteroaryl including optionally substituted variants of the following residues: pyridine, pyrrole, furan, thiophene, imidazole, oxazole, and thiazole. In some embodiments, when Z is an optionally substituted heteroatom, it is selected from the group consisting of $NO_2$, $SO_3H$, $OR_{11}$ where $R_{11}$ is selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl. In the compound of Formula (II), n may be 0, 1, 2, 3, 4, 5, 6, 7, 8, 9, or 10. In some embodiments n is less than 5. In one embodiment n is 4.

Each X may be separately selected from the group consisting of F, Cl, Br, and I.

$R_{10}$ may be selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Each bond represented by a dashed and solid line in the structure of Formula (II) may either be a carbon-carbon single bond or a carbon-carbon double bond and if a carbon-carbon double bond, may have either cis or trans configuration.

Some embodiments of the compound of Formula (II) are represented by Formula (IIb):

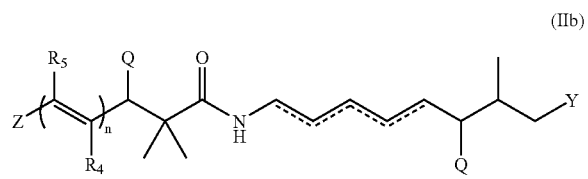

(IIb)

The configuration of each unit n in the compound of Formula (IIb) may be separately selected from cis or trans.

In another embodiment, the invention provides compounds, pharmaceutical compositions, methods of producing compounds, and methods of treating cancer and microbial infections by administering compounds and compositions, wherein the compounds are represented by Formula (III):

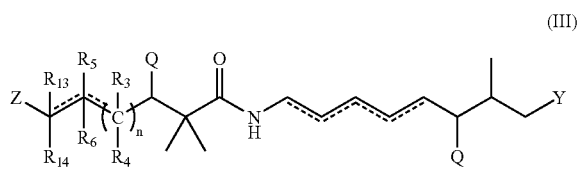

(III)

In the compound of Formula (III), $R_3$, $R_4$, $R_{13}$, and $R_{14}$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, O, and S or may each be separately absent when necessary to accommodate double bonds. $R_5$ and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, O, and S or may each be separately absent when necessary to accommodate double bonds. Y has the following structures:

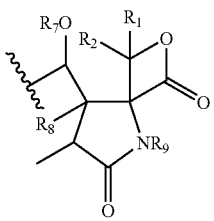

where $R_1$, $R_2$, and $R_8$ may each be separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

In the compound of Formula (III), n may be 0, 1, 2, 3, 4, 5, 6, 7, 8, 9, or 10. In some embodiments n is less than 7. In one embodiment n is 6.

Z may be selected from the following structures:

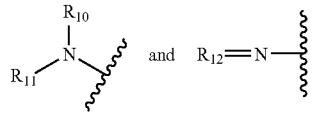

$R_{10}$ and $R_{11}$ may each be separately be selected from the group consisting of H, optionally substituted saturated $C_1$–$C_{24}$ alkyl, optionally substituted unsaturated $C_1$–$C_{24}$ alkenyl, O, and S. $R_{12}$ can be an optionally substituted unsaturated $C_1$–$C_{24}$ alkenyl. In some embodiments, $R_{10}$, $R_{11}$, or $R_{12}$ may optionally be bound to $R_5$ or $R_6$ to form a nitrogen containing heterocyclic ring. Each bond represented by a dashed and solid line in the structure of Formula (III) may either be a carbon-carbon single bond or a carbon-carbon double bond and if a carbon-carbon double bond, may have either cis or trans configuration. Where the valence of a carbon atom containing a bond represented by a dashed and solid line would exceed four if the bond were a carbon-carbon double bond, it is to be understood that the bond can only be a carbon-carbon single bond. Where n is greater than 1, it is to be understood that each unit n is bonded to any adjacent units n via carbon-carbon single bonds or carbon-carbon double bonds with either cis or trans configuration.

In another embodiment, the compounds of Formulas (I), (II), and (III) have the structure of Formula (IV):

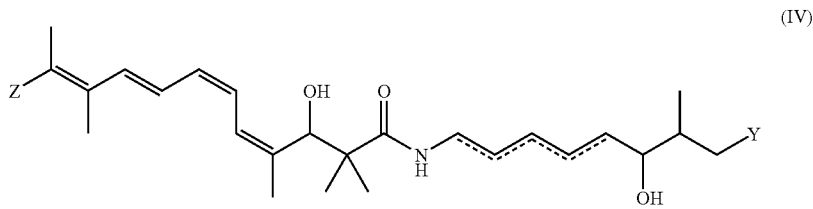

(IV)

In another embodiment, the compound of Formula (IV) has the structure of Formula (V):

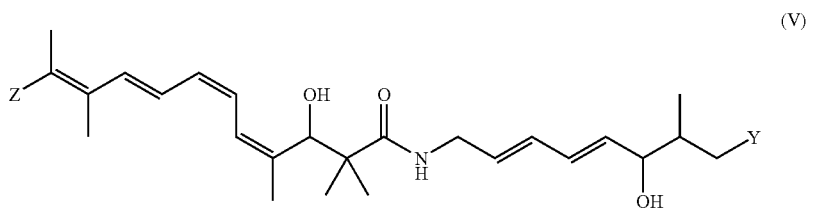

(V)

In the structures of Formulas (IV) and (V), Z and Y have the same meanings as described above for Formulas (I), (II), and (III). In one particular embodiment, the compound of Formula (V) has the structure of Formula (VI):

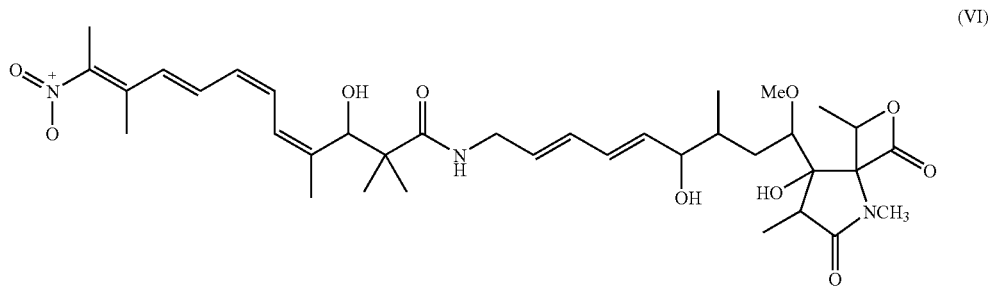

(VI)

In some embodiments, a method is provided for treating an individual infected with a bacteria. In some embodiments, the method includes administering to the individual a compound selected from the compounds of Formulae I through VI or their acid-addition salts or pro-drug esters. In some embodiments, the bacteria is a gram positive bacteria such as *Staphylococcus aureus* (MSSA), *Staphylococcus aureus* (MRSA), *Streptococcus pneumonias, Enterococcus faecalis* (VSE), or *Enterococcus faecium* (VRE). In some embodiments, the bacteria is *Escherichia coli*, including either drug sensitive or drug resistant strains.

In some other embodiments, a method is provided for treating an individual with cancer. In some embodiments, the method includes administering to the individual a compound selected from the compounds of Formulae I through VI or their acid-addition salts or pro-drug esters. In some embodiments, the method includes the step of contacting a cancer cell with a compound selected from the compounds of Formulae I through VI or their acid-addition salts or pro-drug esters. In some embodiments, the method includes contacting a patient diagnosed with cancer with a compound selected from the compounds of Formulae I through VI or their acid-addition salts or pro-drug esters. In one embodiment, the cancer is a melanoma.

DETAILED DESCRIPTION OF THE PREFERRED EMBODIMENT

Figure 1:
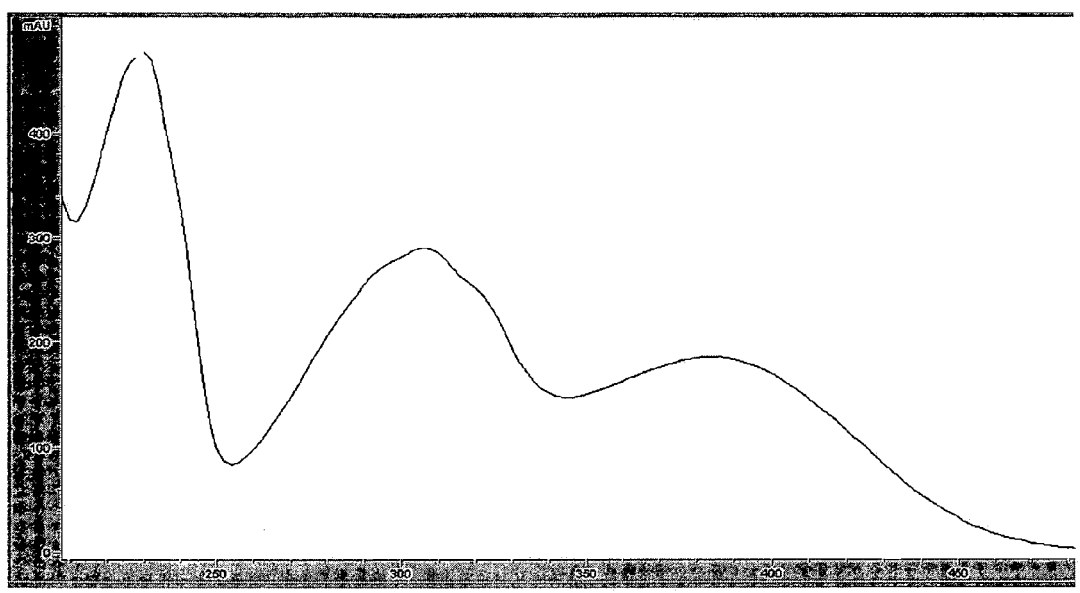
FIG. 1 shows the UV spectrum of the compound of Formula (VI).

Numerous references are cited herein. The references cited herein, including the U.S. patents cited herein, are to be each considered incorporated by reference in their entirety into this specification.

Embodiments of the invention include, but are not limited to providing a method for the preparation of compounds, including novel compounds, including β-lactone/?-lactam compounds and analogs thereof, and to providing a method for producing pharmaceutically acceptable anti-tumor compositions, and anti-infectious disease compositions, for example. The methods can include the compositions in relatively high yield, wherein the compounds and/or their derivatives are among the active ingredients in these compositions. Other embodiments relate to providing novel compounds not obtainable by currently available methods. Furthermore, some embodiments relate to methods of treating cancer and infectious diseases. In preferred embodiments animal cancer and animal infectious diseases are treated by administering an effective amount of a member of a class of new compounds. Preferred embodiments relate to the compounds and methods of making and using such compounds disclosed herein, but these objectives are not necessarily met in all embodiments of the present invention.

In one embodiment, the invention provides compounds, pharmaceutical compositions, methods of producing compounds, and methods of treating cancer and microbial infections by administering compounds and compositions, wherein the compounds are represented by Formula (I):

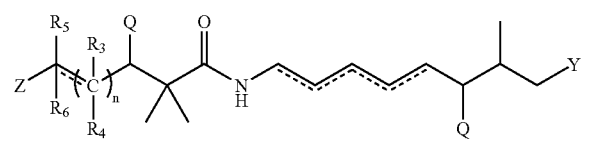

(I)

In the compound of Formula (I), $R_3$, $R_4$, $R_5$, and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfo- nyl, carboxy, cyano, halogenated alkyl including polyhalogenated alkyl, or absent when necessary to accommodate double bonds. Y has the structure of the following formula:

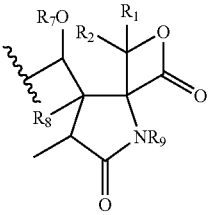

where $R_1$, $R_2$, and $R_8$ may each be separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

In the compound of Formula (I), n can be 0, 1, 2, 3, 4, 5, 6, 7, 8, 9, or 10. In some embodiments n is less than 8. In one embodiment n is 7.

Any electron withdrawing group can be selected for Z. For example, Z can be selected from the group consisting of optionally substituted heteroatom, $CX_3$, $CHX_2$, $CH_2X$, CN, C(O)X, C(O)OR$_{10}$, C(O)R$_{10}$, and X, where each X is separately selected from the group consisting of F, Cl, Br, and I. Z can also be selected from heterocyclic electron withdrawing groups such as optionally substituted aryl or heteroaryl including optionally substituted variants of the following: pyridine, pyrrole, furan, thiophene, imidazole, oxazole, and thiazole. In some embodiments, when Z is an optionally substituted heteroatom, it is selected form the group consisting of NO$_2$, SO$_3$H, and OR$_{11}$ where R$_{11}$ is selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl. When Z is an optionally substituted variant of oxazole, then n is preferably not 6.

R$_{10}$ may be selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Each bond represented by a dashed and solid line in the structure of Formula (I) may either be a carbon-carbon single bond or a carbon-carbon double bond and if a carbon-carbon double bond, may have either cis or trans configuration. Where n is greater than 1, it is to be understood that each unit n is bonded to any adjacent units n via carbon-carbon single bonds or carbon-carbon double bonds with either cis or trans configuration.

In another embodiment, the invention provides compounds, pharmaceutical compositions, methods of producing compounds, and methods of treating cancer and microbial infections by administering compounds and compositions, wherein the compounds are represented by Formula (II):

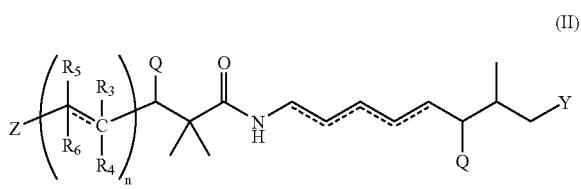

(II)

In the compound of Formula (II), $R_3$, $R_4$, $R_5$, and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, or absent when necessary to accommodate double bonds. Y has the following structure:

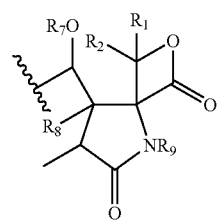

where $R_1$, $R_2$, and $R_8$ may each be separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

Any suitable electron withdrawing group can be selected for Z. For example, Z can be selected from the group consisting of optionally substituted heteroatom, $CX_3$, $CHX_2$, $CH_2X$, CN, C(O)X, C(O)O$R_{10}$, C(O)$R_{10}$, X, as defined herein, and optionally substituted aryl or heteroaryl including optionally substituted variants of the following residues: pyridine, pyrrole, furan, thiophene, imidazole, oxazole, and thiazole. In some embodiments, when Z is an optionally substituted heteroatom, it is selected from the group consisting of $NO_2$, $SO_3H$, and O$R_{11}$ where $R_{11}$ is selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl. In the compound of Formula (II), n may be 0, 1, 2, 3, 4, 5, 6, 7, 8, 9, or 10. In some embodiments n is less than 5. In one embodiment n is 4.

Each X may be separately selected from the group consisting of F, Cl, Br, and I.

$R_{10}$ may be selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Each bond represented by a dashed and solid line in the structure of Formula (II) may either be a carbon-carbon single bond or a carbon-carbon double bond and if a carbon-carbon double bond, may have either cis or trans configuration.

Some embodiments of the compound of Formula (II) are represented by Formula (IIb):

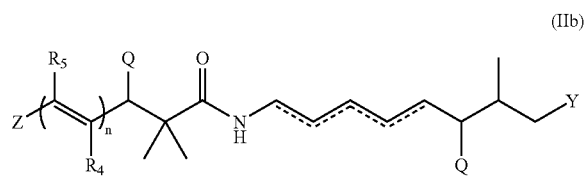

(IIb)

The configuration of each unit n in the compound of Formula (IIb) may be separately selected from cis or trans In one embodiment, the invention provides compounds, pharmaceutical compositions, methods of producing compounds, and methods of treating cancer and microbial infections by administering compounds and compositions, wherein the compounds are represented by Formula (III):

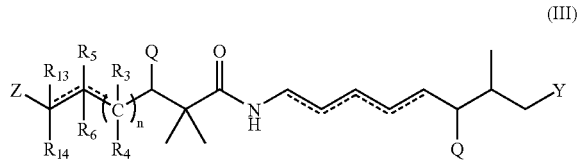

(III)

In the compound of Formula (III), $R_3$, $R_4$, $R_{13}$, and $R_{14}$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, or absent when necessary to accommodate double bonds. $R_5$ and $R_6$ may each be separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, O, and S or may each be separately absent when necessary to accommodate double bonds. Y has the structure of the following formula:

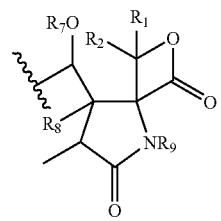

where $R_1$, $R_2$, and $R_8$ may be each separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. $R_7$ and $R_9$ may each be separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, alkyloxycarbonyl, aryloxycarbonyl, cycloalkyl, cycloalkenyl, aryl, heteroaryl, arylalkyl, carbonyl, aminocarbonyl, phenyl, carboxy, and halogenated alkyl including polyhalogenated alkyl.

Q is an optionally substituted heteroatom. In one embodiment, Q is optionally substituted O, S, or N. In one embodiment, Q is OH or SH.

In the compound of Formula (III), n may be 0, 1, 2, 3, 4, 5, 6, 7, 8, 9, or 10. In some embodiments n is less than 7. In one embodiment n is 6.

Z may be selected from the following structures:

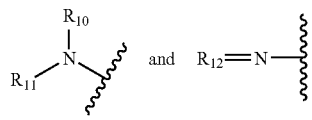

$R_{10}$ and $R_{11}$ may each be separately be selected from the group consisting of H, optionally substituted saturated $C_1$–$C_{24}$ alkyl, optionally substituted unsaturated $C_1$–$C_{24}$ alkenyl, O, and S. $R_{12}$ can be an optionally substituted unsaturated $C_1$–$C_{24}$ alkenyl. In some embodiments, $R_{10}$, $R_{11}$, or $R_{12}$ may optionally be bound to $R_5$ or $R_6$ to form a nitrogen containing heterocyclic ring. Each bond represented by a dashed and solid line in the structure of Formula (III) may either be a carbon-carbon single bond or a carbon-carbon double bond and if a carbon-carbon double bond, may have either cis or trans configuration. Where the valence of a carbon atom containing a bond represented by a dashed and solid line would exceed four if the bond were a carbon-carbon double bond, it is to be understood that the bond can only be a carbon-carbon single bond. Where n is greater than 1, it is to be understood that bonds between carbons in each unit n may be either carbon-carbon single bonds or carbon-carbon double bonds with either cis or trans configuration.

In one embodiment, the compound of Formula (III) has the structure:

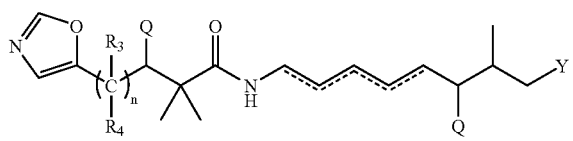

where n may be 1, 2, 3, 4, 5, 6, 8, 9, or 10 and where n is greater than 1, it is to be understood that bonds between carbons in each unit n may be either carbon-carbon single bonds or carbon-carbon double bonds with either cis or trans configuration.

In one embodiment, the compounds of Formulas (I), (II), and (III) have the structure of Formula (IV):

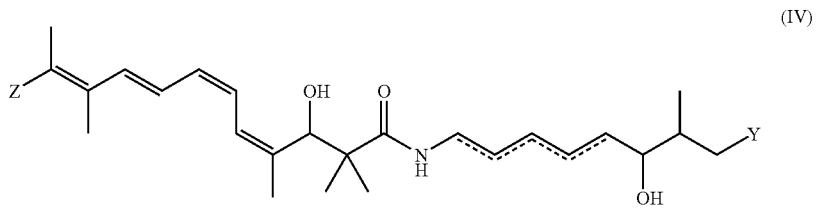

(IV)

In one embodiment, the compound of Formula (IV) has the structure of Formula (V):

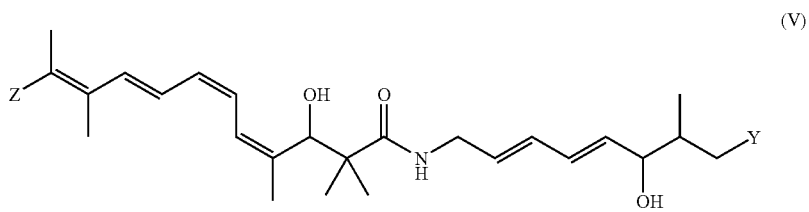

(V)

In the structures of Formulas (IV) and (V), Z and Y have the same meanings as described above for Formulas (I), (II), and (III). In one particular embodiment, the compound of Formula (V) has the structure of Formula (VI):

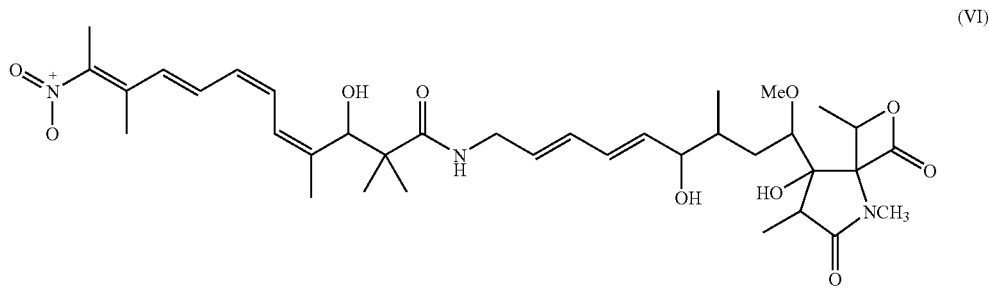

(VI)

The invention also provides pharmaceutically acceptable salts and pro-drug esters of the compounds of Formulas (I)–(VI) and provides methods of obtaining and purifying such compounds by the methods disclosed herein.

The term "pro-drug ester," especially when referring to a pro-drug ester of the compounds of Formulas (I)–(VI) obtained by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as prodrugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo- 1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as pro-drugs for compounds containing carboxyl groups); both of which are incorporated herein by reference in their entireties.

The term "pharmaceutically acceptable salt," as used herein, and particularly when referring to a pharmaceutically acceptable salt of a compound, including compounds of Formulas (I)–(VI) obtained by the methods disclosed herein, refers to any pharmaceutically acceptable salts of a compound, and preferably refers to an acid addition salt of a compound. Some examples of pharmaceutically acceptable salts are the alkali metal salts (sodium or potassium), the alkaline earth metal salts (calcium or magnesium), or ammonium salts derived from ammonia or from pharmaceutically acceptable organic amines, for example $C_1$–$C_7$ alkylamine, cyclohexylamine, triethanolamine, ethylenediamine or tris-(hydroxymethyl)-aminomethane. With respect to compounds obtained by the method of the invention that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compounds of Formulas (I)–(VI) obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

The term "halogen atom," as used herein, means any one of the radio-stable atoms of column 7 of the Periodic Table of the Elements, i.e., fluorine, chlorine, bromine, or iodine, with fluorine and chlorine being preferred.

The term "alkyl," as used herein, means any unbranched or branched, substituted or unsubstituted, saturated hydrocarbon, with $C_1$–$C_6$ unbranched, saturated, unsubstituted hydrocarbons being preferred, with methyl, ethyl, isobutyl, and tert-butyl being most preferred. Among the substituted, saturated hydrocarbons, $C_1$–$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred. The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Patent No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. The other above-listed patents also provide standard definitions for the term "substituted" that are well-understood by those of skill in the art. The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$–$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The substituted aryls and heteroaryls can be substituted with any substituent, including those described above and those known in the art.

The term "alkoxy" refers to any unbranched, or branched, substituted or unsubstituted, saturated or unsaturated ether, with $C_1$–$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

The terms "purified," "substantially purified," and "isolated" as used herein refer to the compounds of the invention being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

Throughout this disclosure, all bonds represented by a dashed and solid line may either be a carbon-carbon single bond or a carbon-carbon double bond and if a carbon-carbon double bond, may have either cis or trans configuration.

The compounds of Formulas (I)–(VI) may be obtained and purified as set forth below.

Producing Organisms

One microorganism which may be used for the production of the compounds of the present invention is a strain isolated from a marine sediment sample collected in Scripps Canyon, Calif. The culture (strain NPS007994) was deposited on Jan. 7, 2004 with the American Type Culture Collection (ATCC) in Rockville, Md. and assigned the ATCC patent deposition number PTA-5747. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce compounds of the present invention.

Fermentation of Strain NPS007994

The production of compounds of the present invention may be carried out by cultivating strain NPS007994 in a suitable nutrient medium under conditions described herein, preferably under submerged aerobic conditions, until a substantial amount of compounds are detected in the fermentation; harvesting by extracting the active components from the mycelial growth with a suitable solvent; concentrating the solution containing the desired components; then subjecting the concentrated material to chromatographic separation to isolate the compounds from other metabolites also present in the cultivation medium.

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 300 rpm, preferably at 150 rpm to 250 rpm, for example.

Growth of the microorganisms may be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources may be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottton-seed meal, fish meal, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

The following is one exemplary fermentation protocol that can be utilized for preparing a 10 L batch of organisms that include compounds of the present invention:

1. Inoculate the starting culture or the freeze culture into 10 ml seed medium and incubate at 28° C. and 250 rpm for 3 days.

2. Transfer ~5 ml of the above seed culture into 100-ml seed medium in a 500-ml flask. Incubate the flasks at 28° C. and 250 rpm on a rotary shaker for 3 days.

3. Inoculate 5 ml each of the second seed culture into 10 500-ml flasks containing 100 ml seed medium. Incubate these flasks at 28° C. and 250 rpm on a rotary shaker for 3 days.

4. Inoculate 5 ml each of the third seed culture into 100 500-ml flasks containing 100 ml production medium. Incubate these flasks at 28° C. and 250 rpm on a rotary shaker for 4 days.

5. Add ~2 to 3 grams of resin to each flask. Incubate these flasks at 28° C. and 250 rpm on a rotary shaker for additional 3 days.

6. Extract the resin and cell mass with 10 liters of ethyl acetate. The extract is dried in vacuo and then compounds of the present invention are isolated.

Compound Purification

Pure compounds can be isolated from the fermentation product by any purification means known to those skilled in the art. One such technique is the use of HPLC chromatography as described below:

Column: ACE 5 C18-HL
Dimensions: 15 cm×21 mm ID
Flow rate: 14.5 ml/min
Detection: UV DAD
Solvent: Gradient of 0% Acetonitrile, 100% $H_2O$ to 100% Acetonitrile (25 min.)

The fractions containing a compound of interest can be further purified using semi-preparative HPLC method described as follows. Three mg is dissolved in MeOH (200 µl) and this solution is injected on the HPLC column using the chromatography conditions described below:

Column: ACE 5 C18-HL
Dimensions: 10 mm×250 mm ID
Flow rate: 3 ml/min
Detection: UV DAD
Solvent: Gradient of 40% MeOH, 60% $H_2O$ to 100% MeOH (30 min)

Activity

The compounds of the present invention exhibit antimicrobial and/or anti-cancer activity. Results from antimicrobial screens are shown below in Table 2 in Example 4. For example, the compounds exhibit high activity against bacteria, including against gram positive bacterial strains. Results from anti-cancer activity are shown below in Table 3 in Example 5.

Pharmaceutical Compositions

Embodiments of the present invention also relate to the compounds disclosed herein used in pharmaceutical compositions. The compounds can optionally and preferably produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

Compositions of the compounds described herein may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art. See, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties.

Further disclosed herein are various pharmaceutical compositions well known in the pharmaceutical art for uses that include intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440–50 (2001)) or hydrogels (Mayer et al., *Ophthalmologica*, 210(2):101–3 (1996)); ophthalmic ointments; ophthalmic suspensions, such as microparticulates, drug-containing small polymeric particles that are suspended in a liquid carrier medium (Joshi, A., *J Ocul. Pharmacol.*, 10(1):29–45 (1994)), lipid-soluble formulations (Alm et al., *Prog. Clin. Biol. Res.*, 312:447–58 (1989)), and microspheres (Mordenti, *Toxicol. Sci.*, 52(1):101–6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

When used as an anti-cancer or anti-microbial/infectious disease compound, the compounds of the present invention or compositions including these compounds can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the cancer/tumor is also contemplated, either before or after tumor resection, as are controlled release formulations, depot formulations, and infusion pump delivery.

Methods of Administration

The present invention also encompasses methods for making and for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the β-lactone/ ?-lactam and analog composition required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions may be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds disclosed herein, including cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-cancer agent, a tumor-growth-inhibiting compound, or antimicrobial, the compounds disclosed herein may be administered by either oral or a non-oral pathways. When administered orally, the compounds can be administered in capsule, tablet, granule, spray, syrup, or other such form. When administered non-orally, the compounds can be administered as an aqueous suspension, an oily preparation or the like or as a drip, suppository, salve, ointment or the like, when administered via injection, subcutaneously, intraperitoneally, intravenously, intramuscularly, intradermally, or the like. Similarly, the compounds may be administered topically, rectally, or vaginally, as deemed appropriate by those of skill in the art for bringing the compound of the invention into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

When used as an anti-cancer agent, an anti-tumor agent, or as an antimicrobial, the compound may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or, less preferably, over two to about ten times per day. Alternatively and also preferably, the compounds of the invention may preferably be administered in the stated amounts continuously by, for example, an intravenous drip. Thus, for a patient weighing 70 kilograms, the preferred daily dose of the active ingredient would be about 0.0007 mg/kg/day to about 35 mg/kg/day, and more preferable, 0.007 mg/kg/day to about 0.035 mg/kg/day. Nonetheless, as will be understood by those of skill in the art, in certain situations it may be necessary to administer the compounds of the invention in amounts that excess, or even far exceed, the above-stated, preferred dosage range to effectively and aggressively treat particularly aggressive microbes or tumors.

To formulate the dosage including the compounds disclosed herein as a tumor-growth-inhibiting compound or antimicrobials, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyiacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound of the invention, particularly when the compound is to be administered orally.

The compositions disclosed herein in pharmaceutical compositions may also comprise a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the invention, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions may be formulated and administered either systemically or locally. A variety of techniques for formulation and administration may be found in Remington's Pharmaceutical Sciences, 18th ed., Mack Publishing Co., Easton, Pa. (1990).

To formulate the compounds of the present invention as a tumor-growth-inhibiting, anticancer compound, or antimicrobial, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyiacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound produced by the method of the invention, particularly when the compound is to be administered orally.

In the case of using the anti-tumor, anti-cancer, or antimicrobial produced by methods of the invention as a biochemical test reagent, the compound produced by methods of the invention inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the invention for use as an anti-microbial, anti-cancer, or anti-tumor compound is generally in the range of about 1 to about 100 μg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

The following non-limiting examples are meant to describe the preferred methods of the invention using certain preferred embodiments of the invention. Variations in the details of the particular methods employed and in the precise chemical compositions obtained will undoubtedly be appreciated by those of skill in the art.

EXAMPLE 1

Fermentation Protocol

Strain NPS007994 was grown in a 40 ml tube containing 10 ml of vegetative medium consisting of the following per liter of sea water: starch, 10 g; yeast extract, 4 g; and peptone, 2 g. The culture was allowed to incubate for 3 days at 28 degree C. on a rotary shaker operating at 250 rpm. The vegetative culture was mixed with 2 ml of cryoprotective solution consisting of 500 g glycerol per liter of deionized water. 1.5 ml portions of this mixture were transferred to sterile cryogenic tube (2 ml capacity). The vegetative cultures so obtained were frozen and stored at −80 degree C.

Seed culture for the production of NPS007994 compounds was prepared by transferring 1.5 ml of the cryo-preservative culture to a 40 ml tube containing 10 ml of sterile vegetative medium having the same composition as the above. The seed culture was incubated at 28 degree C. for 3 days on a rotary shaker operating at 250 rpm. Five ml of this seed culture was inoculated into 500 ml flask containing 100 ml of the vegetative medium. The second seed cultures were incubated at 28 degree C. for 3 days on a rotary shaker operating at 250 rpm. Five ml each of the second seed culture was inoculated into ten 500 ml flask containing 100 ml of the vegetative medium. The third seed cultures were incubated at 28 degree C. for 3 days on a rotary shaker operating at 250 rpm. Five ml each of the third seed culture was inoculated into the production medium consisting of the following per liter of sea water: starch 5 g; Hydro Solubles, 4 ml; Menhaden fish meal, 2 g; Kelp powder, 2 g; and chitosan, 2 g. The production culture was incubated at 28 degree C. for 4 days on a rotary shaker operating at 250 rpm. Sterile XAD-16 resin (~2 to 3 grams) was added to each flask. The flasks were returned to the shaker and incubated at 28 degree C. and 250 rpm for additional 3 days. The culture broth was filtered through cheese cloth to recover the cell mass and XAD-16 resin. The cell mass-resin was extracted with 10 liters of ethyl acetate. The extract was dried in vacuo. The dried extract, containing the NPS007994 compounds, was then processed for the recovery of NPS007994 compounds.

EXAMPLE 2

Purification of the Compound of Formula (VI)

Pure compound of Formula (VI) was obtained by HPLC chromatography as follows. Fifty mg of the crude extract from Example 1 was dissolved in MeOH (900 μl) and this solution was injected on the HPLC column using the HPLC chromatography conditions described below:

Column: ACE 5 C18-HL

Dimensions: 15 cm×21 mm ID

Flow rate: 14.5 ml/min

Detection: UV DAD

Solvent: Gradient of 0% Acetonitrile, 100% $H_2O$ to 100% Acetonitrile (25 min)

The compound of Formula (VI) eluted. The fractions containing the compound were further purified using semi-preparative HPLC method described as follows. Three mg was dissolved in MeOH (200 ul) and this solution was injected on the HPLC column using the chromatography conditions described below:

Column: ACE 5 C18-HL

Dimensions: 10 mm×250 mm ID

Flow rate: 3 ml/min

Detection: UV DAD

Solvent: Gradient of 40% MeOH, 60% H$_2$O to 100% MeOH (30 min)

The isolated compound of Formula (VI) was obtained as a bright yellow solid that is qualitatively soluble in CHCl$_3$, MeOH, and DMSO.

EXAMPLE 3

Structural Characterization

Figure 2:
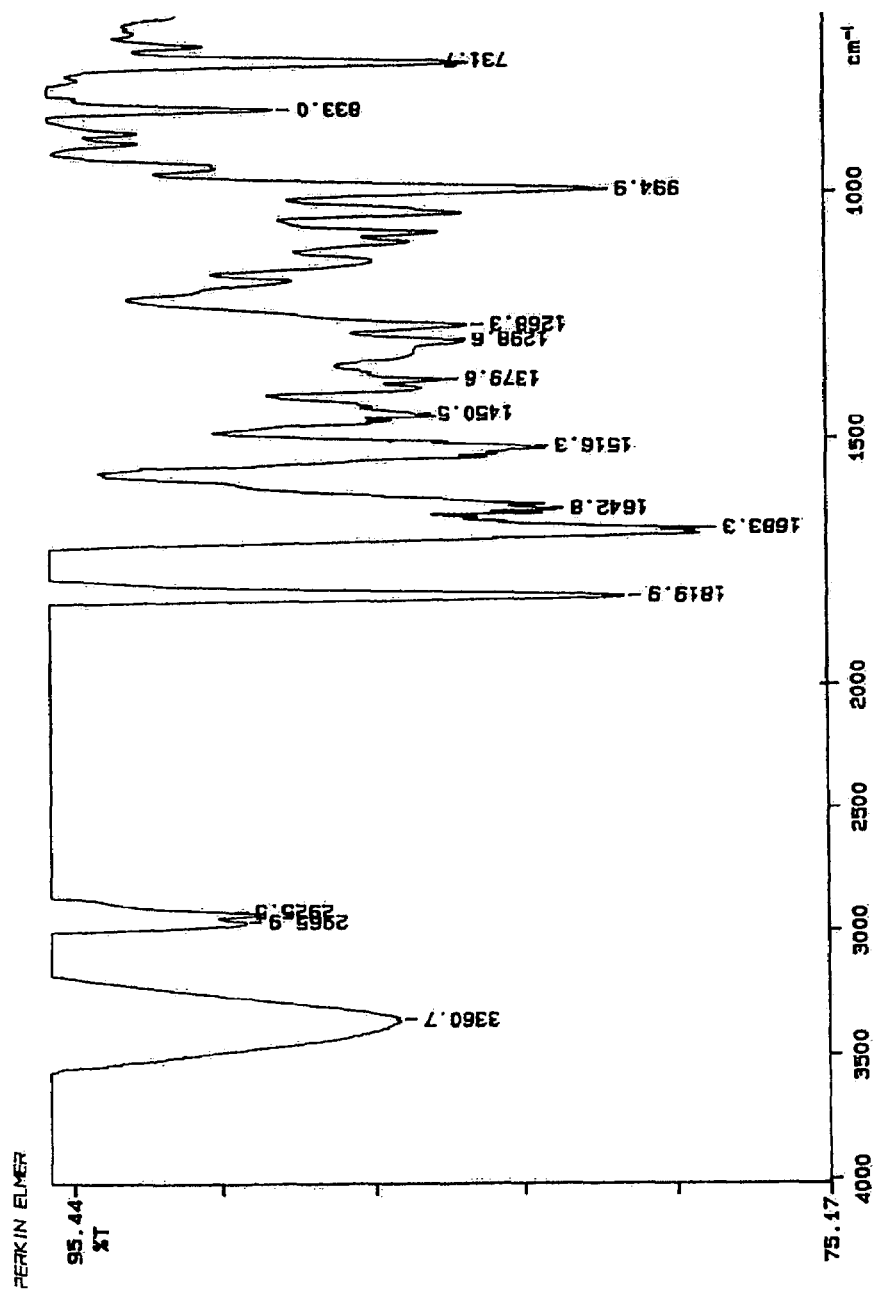
FIG. 2 shows the IR spectrum of the compound of Formula (VI).

The purified compound obtained from Example 2 was characterized as described below:

The UV spectrum was obtained using a diode array detector as the compound eluted on analytical HPLC in acetonitrile/H$_2$O producing the spectrum depicted in FIG. 1. Wavelength maxima were observed at 232, 308 and 380 nm. The UV spectrum was also acquired in methanol using a UV spectrophotometer: UV (MeOH) $\lambda_{max}$ ($\epsilon$) 229 (62794), 306 (39295) and 375 (22110) nm. Maxima in an IR (AgCl) spectrum were observed at 3361 (br), 1820, 1683, 1643 and 1516 cm$^{-1}$. The IR spectrum is depicted in FIG. 2. HRES-IMS (M+H)$^+$688.3814 $\Delta_{calc}$ C$_{36}$H$_{54}$N$_3$O$_{10}$ (688.3809)=0.7 ppm; (M+Na)$^+$710.3638 $\Delta_{calc}$ C$_{36}$H$_{53}$N$_3$O$_{10}$Na (710.3629)= 1.3 ppm; mp 92–95° C.; [$\alpha$]$_D$+75° (c 2×10$^{-5}$, MeOH).

Figure 3:
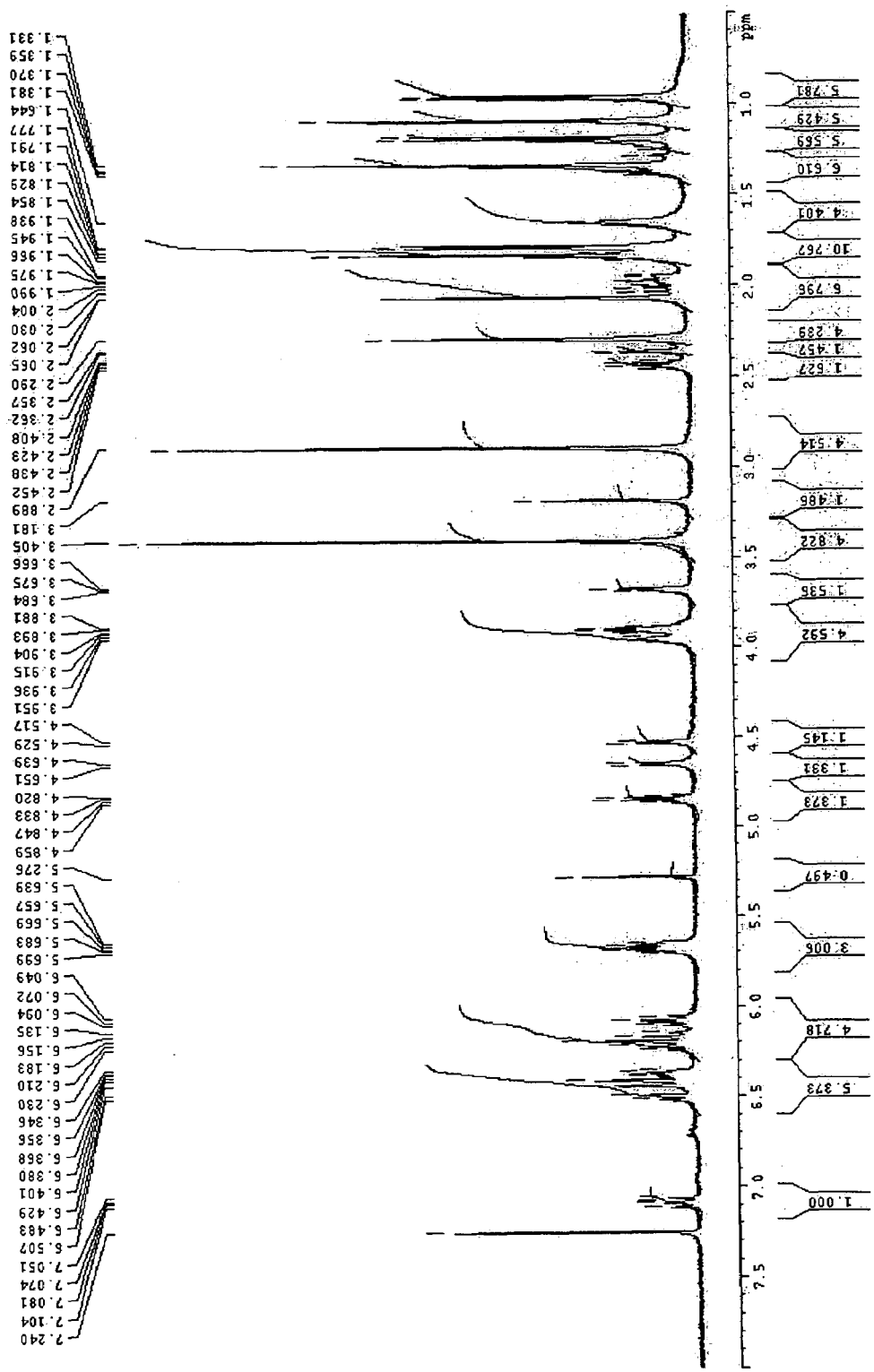
FIG. 3 shows the $^1$H-NMR spectrum of the compound of Formula (VI) in CDCl$_3$.
Figure 4:
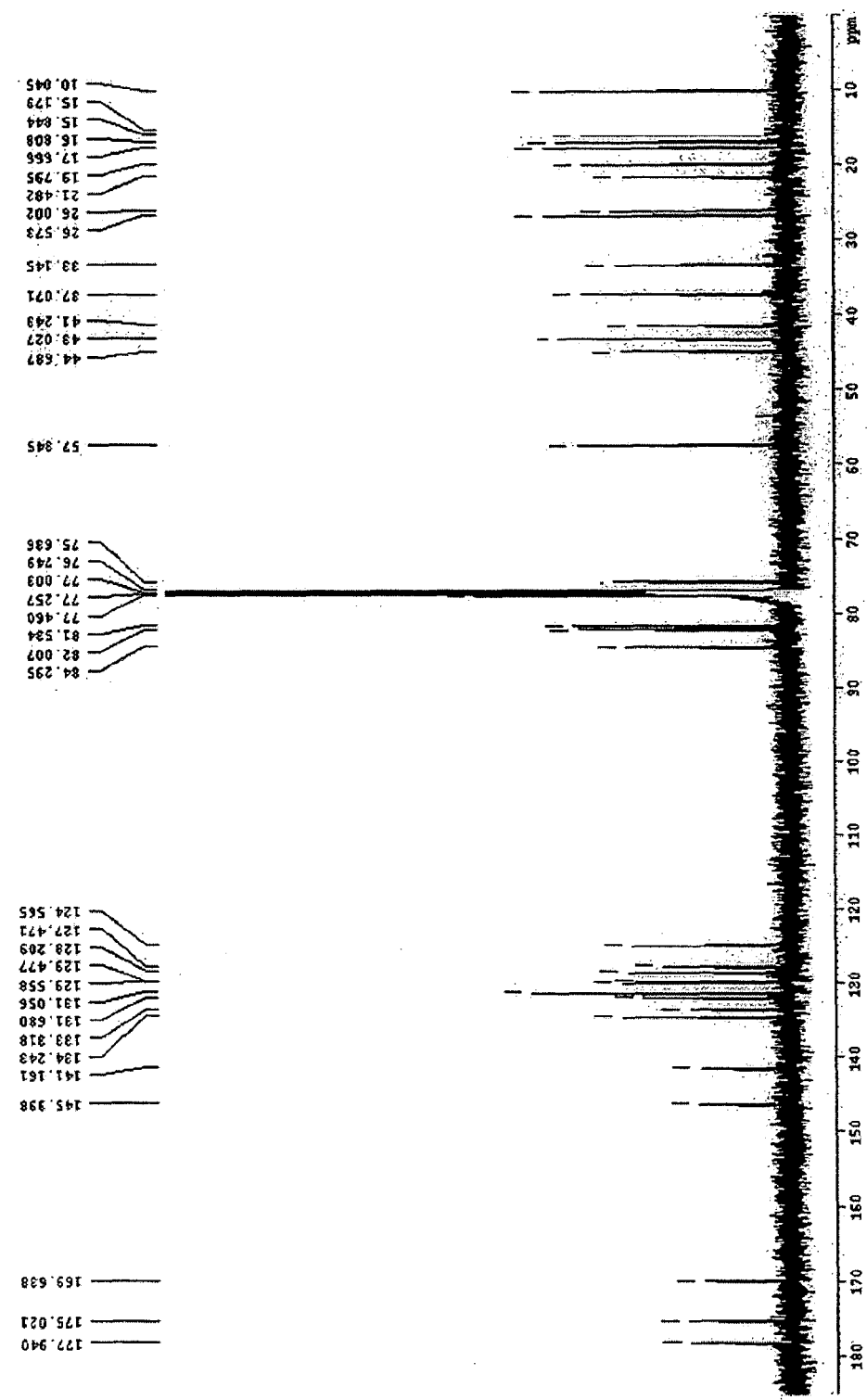
FIG. 4 shows the $^{13}$C-NMR spectrum of the compound of Formula (VI) in CDCl$_3$.

1H-NMR and 13C-NMR spectra in CDCl3 are depicted in FIGS. 3 and 4 respectively. The assignments from these spectra are listed in Table 1 with reference to the following labeled structure:

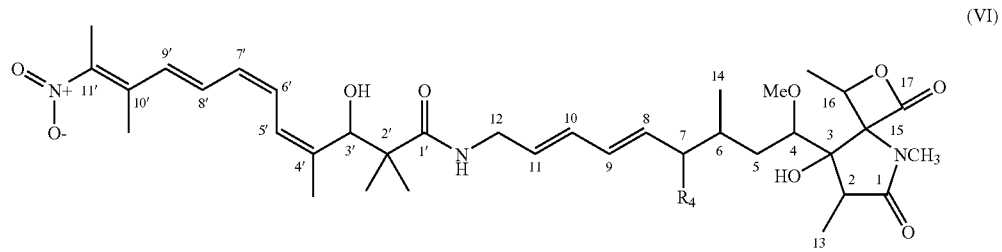

(VI)

Figure 5:
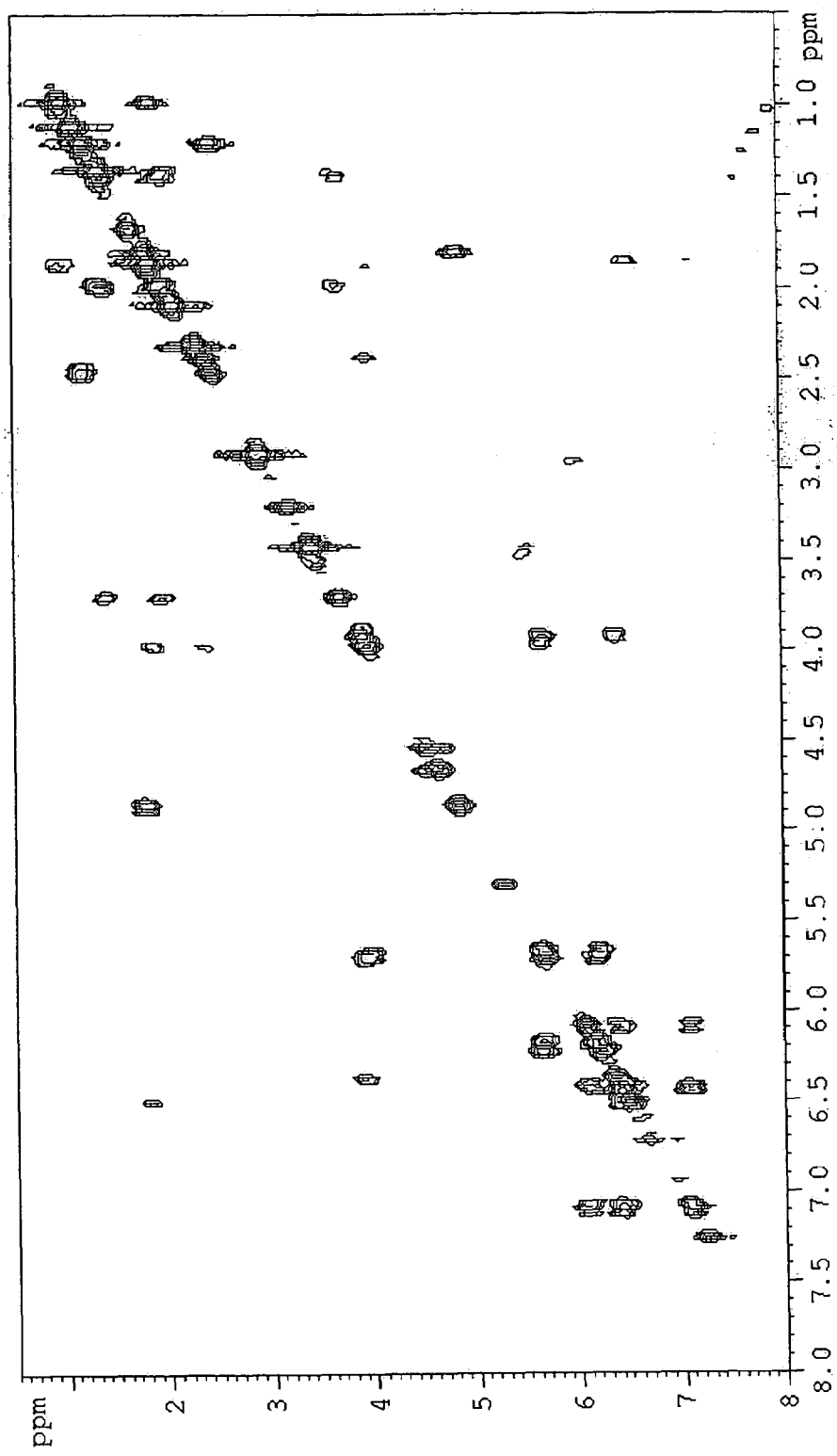
FIG. 5 shows the $^1$H-$^1$H COSY spectrum of the compound of Formula (VI) in CDCl$_3$.
Figure 6:
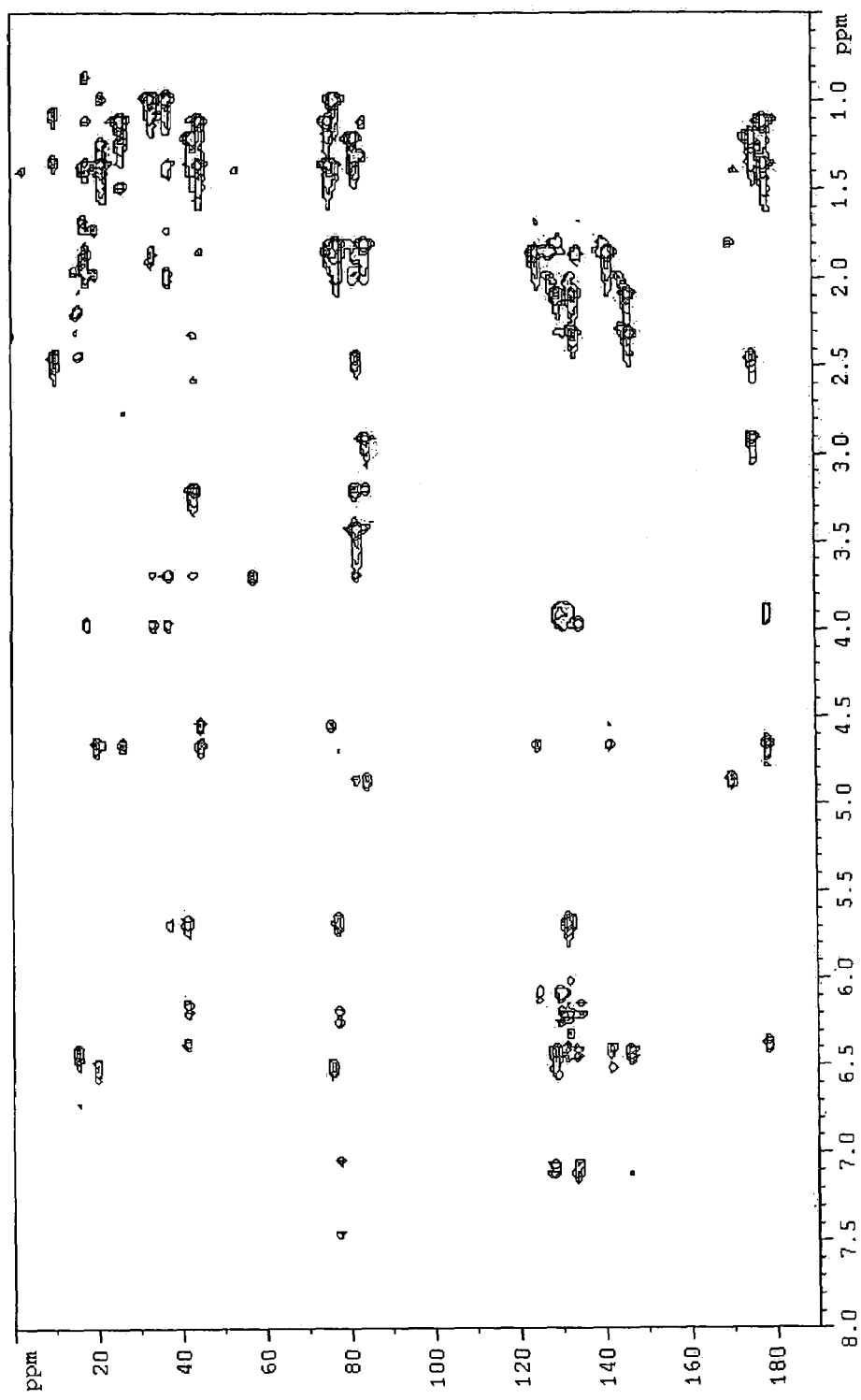
FIG. 6 shows the HMBC spectrum of the compound of Formula (VI) in CDCl$_3$.
Figure 7:
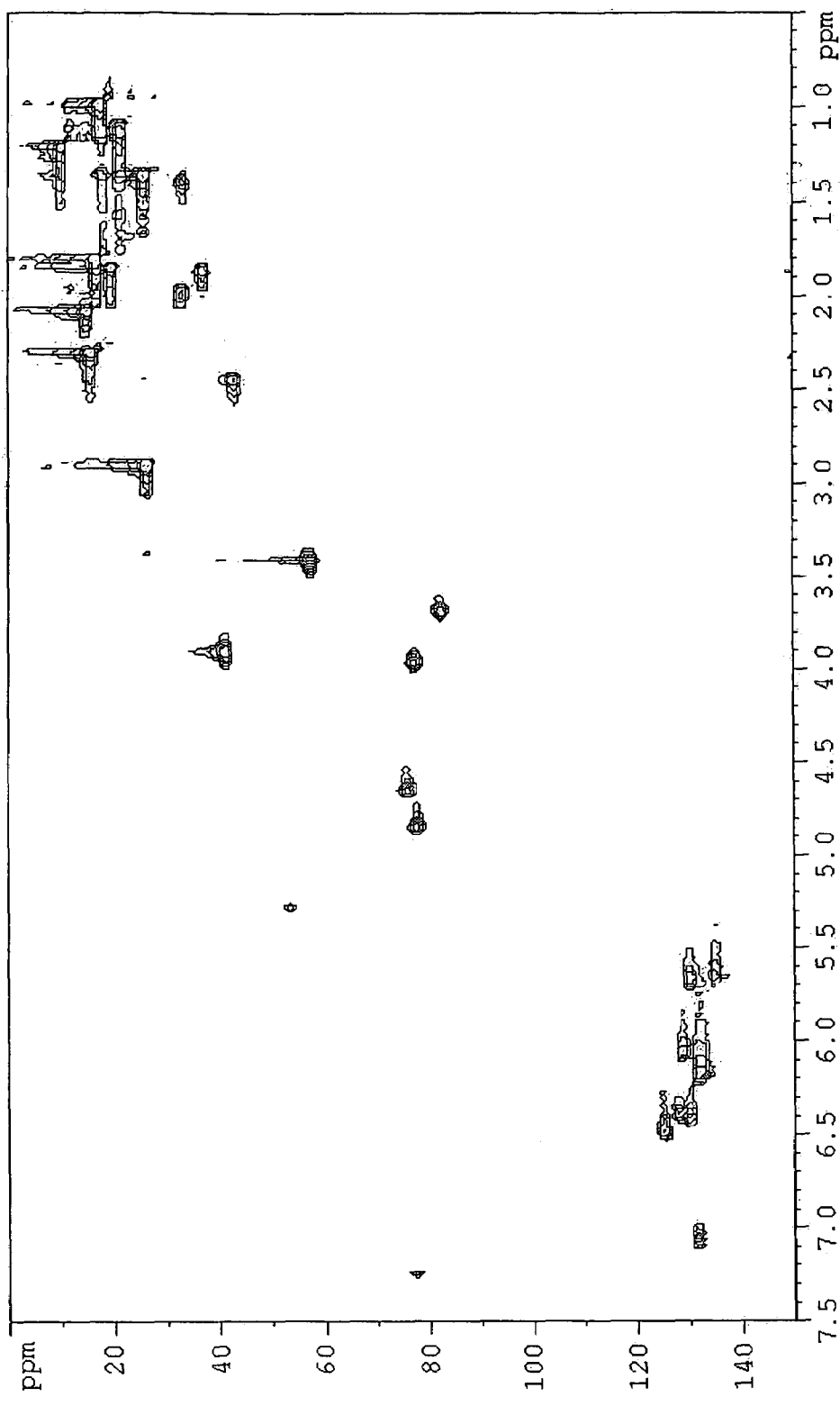
FIG. 7 shows the HMQC spectrum of the compound of Formula (VI) in CDCl$_3$.

The 2D NMR $^1$H-$^1$H COSY, HMBC, and HMQC spectra are depicted in FIGS. 5, 6 and 7, respectively. COSY correlations are depicted with bold lines and HMBC correlations are depicted with arrows as follows:

TABLE 1

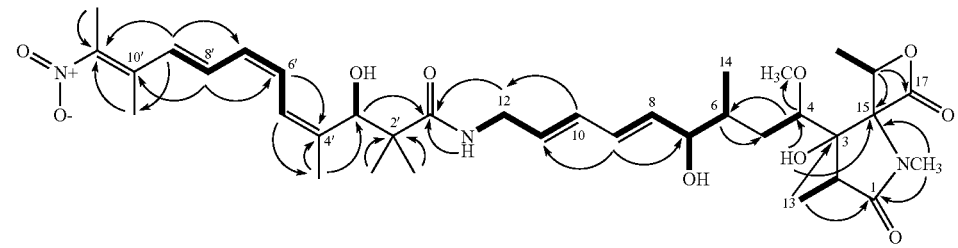

$^1$H and $^{13}$C NMR assignments for Compound of Formula (VI) (CDCl$_3$, 500 MHz)

| Pos | $\delta_C$ | $\delta_H$ (mult, J (Hz)) |
|---|---|---|
| 1 | 175.0 | |
| 2 | 43.0 | 2.43, 1H, q, 7.5 |
| 3 | 81.5 | |
| 4 | 82.0 | 3.67, 1H, t, 4.5 |

TABLE 1-continued

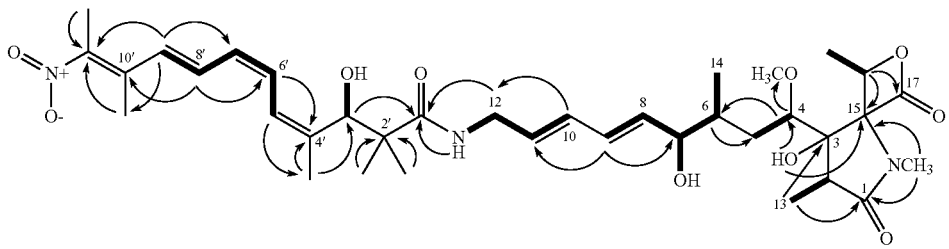

<u>$^1$H and $^{13}$C NMR assignments for Compound of Formula (VI) (CDCl$_3$, 500 MHz)</u>

| Pos | $\delta_C$ | $\delta_H$ (mult, J (Hz)) |
|---|---|---|
| 5 | 33.1 | 1.37, 1H,m |
|  |  | 2.02, 1H, m |
| 6 | 37.1 | 1.85, 1H, m |
| 7 | 76.9 | 3.94, 1H, br t, 6.5 |
| 8 | 134.2 | 5.67, 1H, m |
| 9 | 131.7[a] | 6.21, 1H, m |
| 10 | 131.1[a] | 6.16, 1H, m |
| 11 | 129.5[b] | 5.67, 1H, m |
| 12 | 41.2 | 3.90, 2H, m |
| 13 | 10.0 | 1.18, 3H, d, 7.5 |
| 14 | 17.7 | 0.96, 3H, d, 6.5 |
| 15 | 84.3 |  |
| 16 | 77.5 | 4.84, 1H, q, 7.0 |
| 16-Me | 16.8 | 1.78, 3H, d, 7.0 |
| 17 | 169.6 |  |
| 1' | 177.9 |  |
| 2' | 44.7 |  |
| 2'-Me$_a$ | 21.5 | 1.09, 3H, S |
| 2'-Me$_b$ | 26.0 | 1.33, 3H, S |
| 3' | 75.6 | 4.64, 1H, d, 6.0 |
| 4' | 141.2 |  |
| 4'-Me | 19.8 | 1.83, 3H, br s |
| 5' | 124.6 | 6.49, 1H, d, 12.0 |
| 6' | 127.5 | 6.38, 1H, m |
| 7' | 128.2 | 6.07, 1H,t, 11.5 |
| 8' | 131.8[a] | 7.08, 1H, dd, 11.5, 15 |
| 9' | 129.6[b] | 6.41, 1H, d, 15 |
| 10' | 133.3 |  |
| 10'-Me | 15.2 | 2.06, 3H, br s |
| 11' | 146.0 |  |
| 11'-Me | 15.8 | 2.29, 3H, br s |
| N-Me | 26.6 | 2.89, 3H, S |
| 4-OMe | 57.3 | 3.40, 3H, s |
| NH |  | 6.36, 1H, m |
| 3-OH |  | 3.18, 1H, s |
| 3'-OH |  | 4.52, d, 6.0 |
| 7-OH |  | 2.36, br d, 2.5 |

[a]assignments interchangeable
[b]assignments interchangeable

The 1D and 2D NMR data, taken together, may be understood to suggest the presence of several substructures common to a small family of triene spiro-β-lactone-γ-lactams, including oxazolomycin (Mori, T.; Takahashi, K.; Kashiwabara, M.; Lemura, D.; Iwadare, S.; Shizuri, Y.; Mitomo, R.; Nakano, F.; Matsuzaki, A. *Tetrahedron Lett.* 1985, 26, 1073–1076; which is incorporated herein by reference in its entirety), 16-methyloxazolomycin (Ryu, G.; Hwang, S.; Kim, S. *J. Antibiotics* 1997, 50, 1064–1066; which is incorporated herein by reference in its entirety) and triedimycin B (Ikeda, Y.; Kondo, S.; Naganawa, H.; Hattori, S.; Hamada, M.; Takeuchi, T. *J. Antibiotics* 1991, 44, 453–455; which is incorporated herein by reference in its entirety). The structure of the compound of Formula (VI) from C-1 to C-17, which includes the spiro-β-lactone-γ-lactam bicyclic ring system, across the amide linkage joining C-12 to C-1', and through the C-1' to C-9' carbon chain, which contains the triene conjugated olefin, was similar to 16-methyloxazolomycin and triedimycin B. However, the oxazole ring common to oxazolomycin, 16-methyloxazolomycin, and triedimycin B was absent in the compound of Formula (VI).

Figure 8:
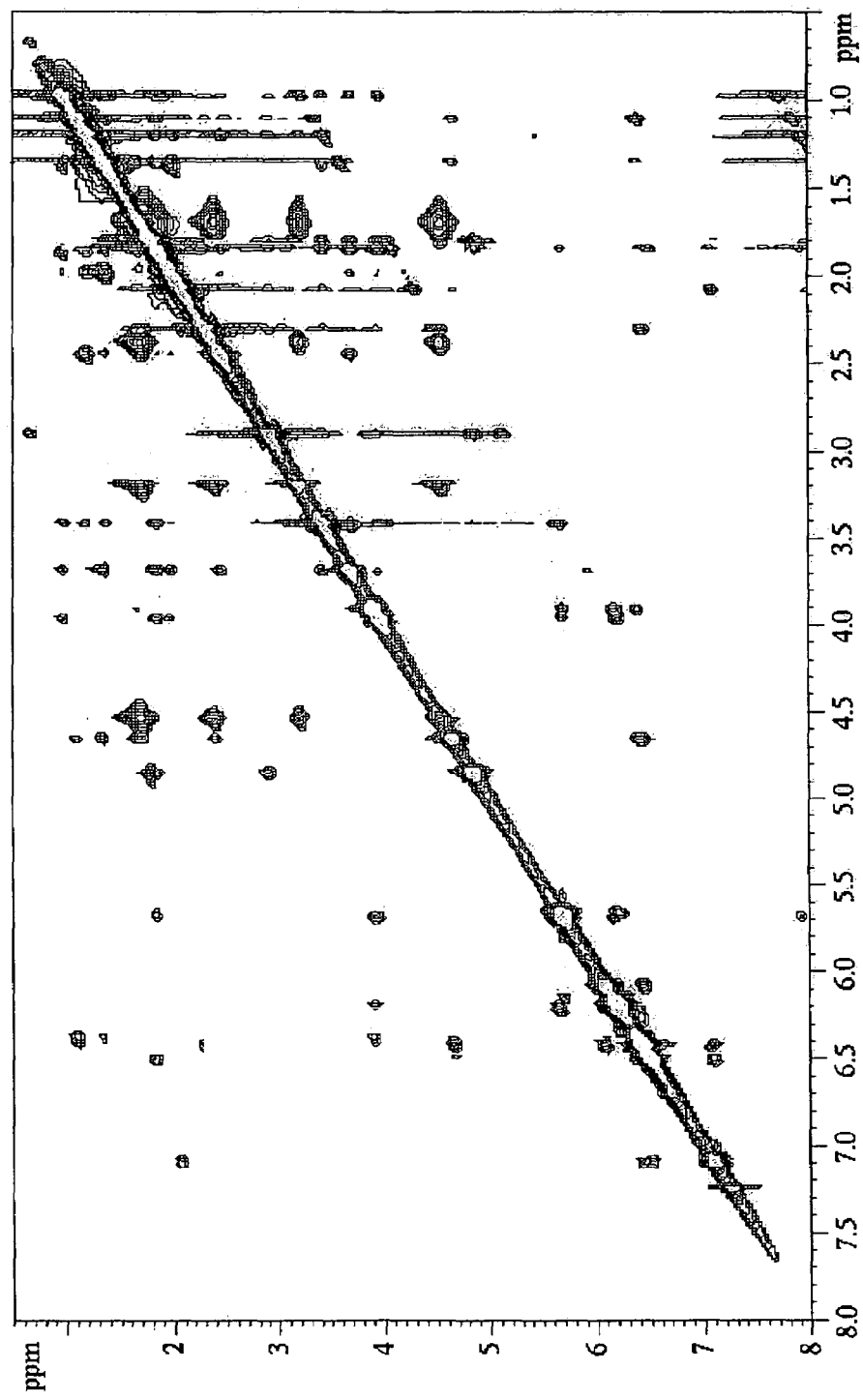
FIG. 8 shows the NOESY spectrum of the compound of Formula (VI) in CDCl$_3$.

Analysis of a series of NOESY (FIG. 8) and HMBC correlations (H-8', H-9', H$_3$-12' and H$_3$-13' to C-10'; H-9' and H$_3$-12' to C-11') indicated that the triene system of the compound of Formula (VI) was extended by an additional double bond that was substituted with two methyl groups. The resulting substructure encompassed all of the required hydrogens and carbons, 2 of the nitrogens, and 8 of the oxygens, leaving only NO$_2$ unaccounted for. The nitro group was therefore placed at the terminal carbon (C-11', δ 146.0), giving rise to a nitro-tetraene conjugated olefin.

The double bond geometries of the tetraene system were established through analysis of proton-proton coupling constants, NOEDS, and NOESY data. The NOESY correlations are depicted with arrows as follows:

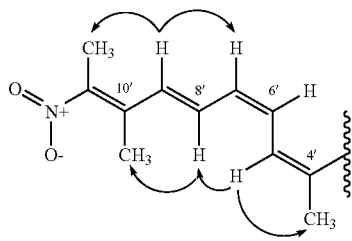

Figure 9:
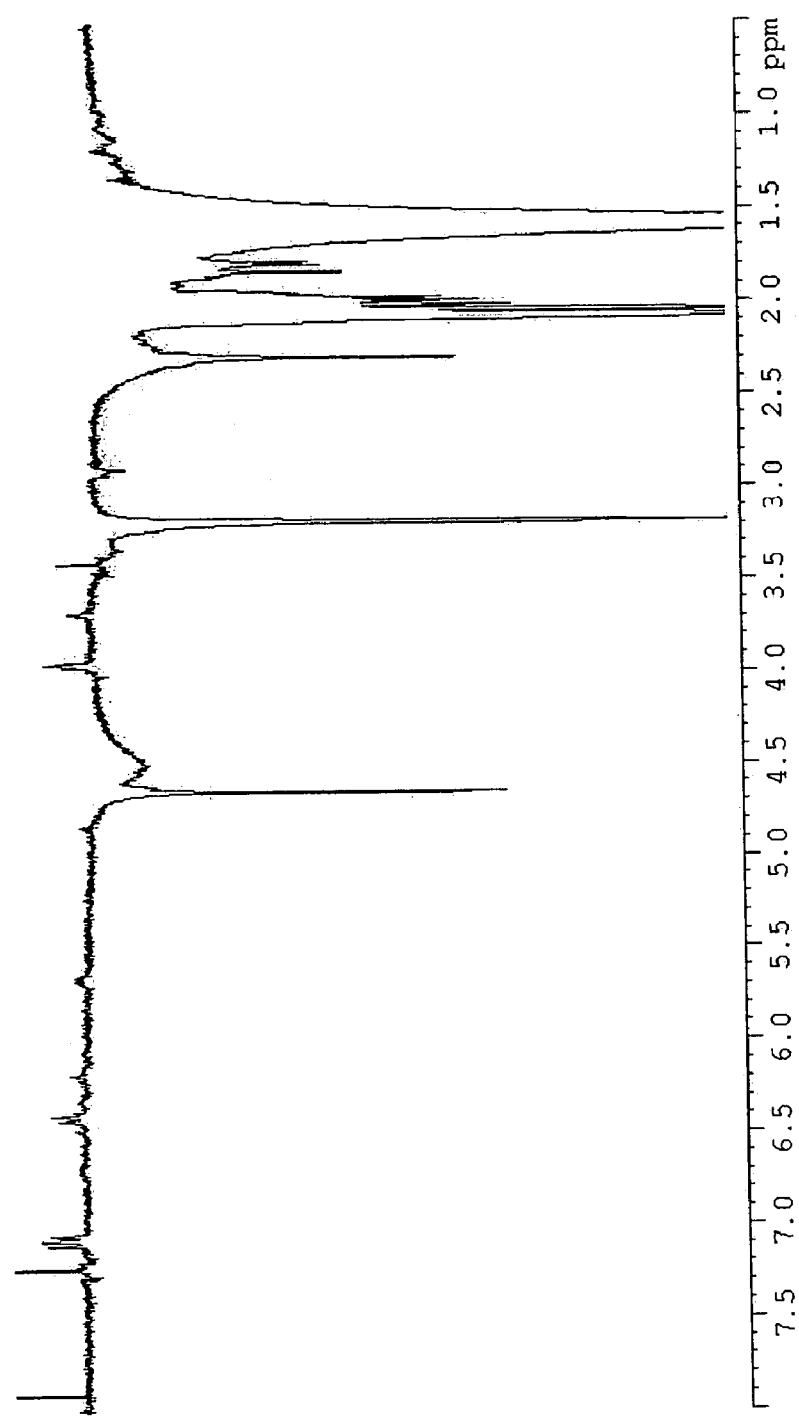
FIG. 9 shows the NOEDS spectrum of the compound of Formula (VI) in CDCl$_3$ irradiated at 2.06 ppm.
Figure 10:
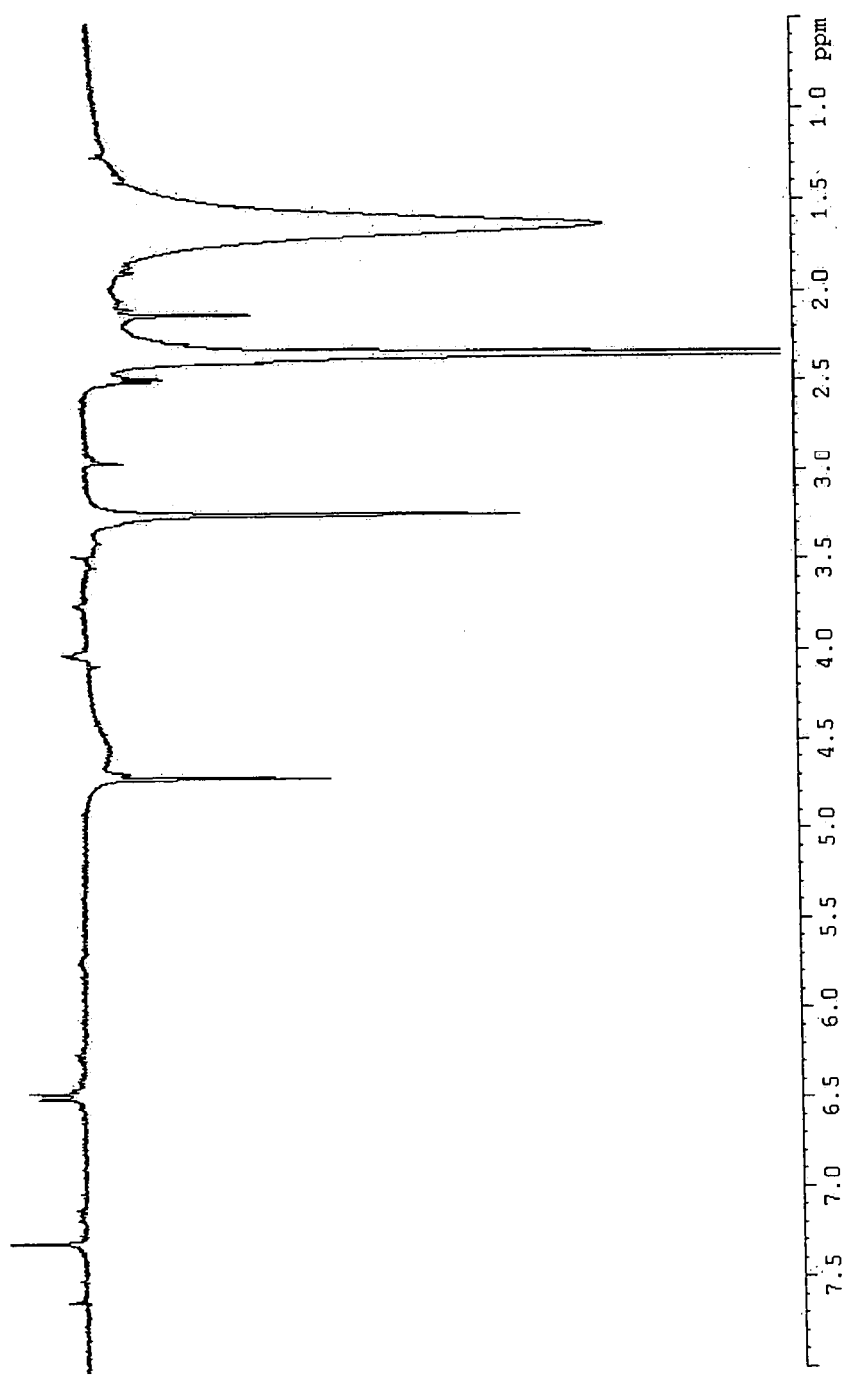
FIG. 10 shows the NOEDS spectrum of the compound of Formula (VI) in CDCl$_3$ irradiated at 2.29 ppm.

The trans geometry of the C-8'/C-9' olefin was supported by large vicinal proton-proton coupling constants for H-8' and H-9' (J=15 Hz). NOESY correlations from H-8' to $H_3$-10'-Me and from H-9' to $H_3$-11'-Me in turn established the trans geometry of the C-10'/C-11' olefin. Independent confirmation of these NOEs was obtained through NOEDS experiments, in which irradiation at $H_3$-10'-Me gave rise to enhancement of the H-8' multiplet (see FIG. 9), while irradiation at $H_3$-11'-Me resulted in enhancement of the H-9' doublet (see FIG. 10). H-9' was further correlated to H-7' in the NOESY spectrum, while H-5' was correlated to H-8'. These data, together with the H-6'/H-7' coupling constant (J=11.5 Hz), established the cis geometry of the C-6'/C-7' olefin. Finally, H-5' was correlated to $H_3$-4'-Me in the NOESY spectrum, indicating that the C-4'/C-5' olefin geometry was cis. Thus, the double bonds of the conjugated triene system from C-4' to C-9' of the compound of Formula (VI) were of identical geometry (cis, cis, trans) to those of oxazolomycin, 16-methyloxazolomycin, and triedimycin B and further extended by one trans (C-10'/C-11') olefin.

Figure 11:
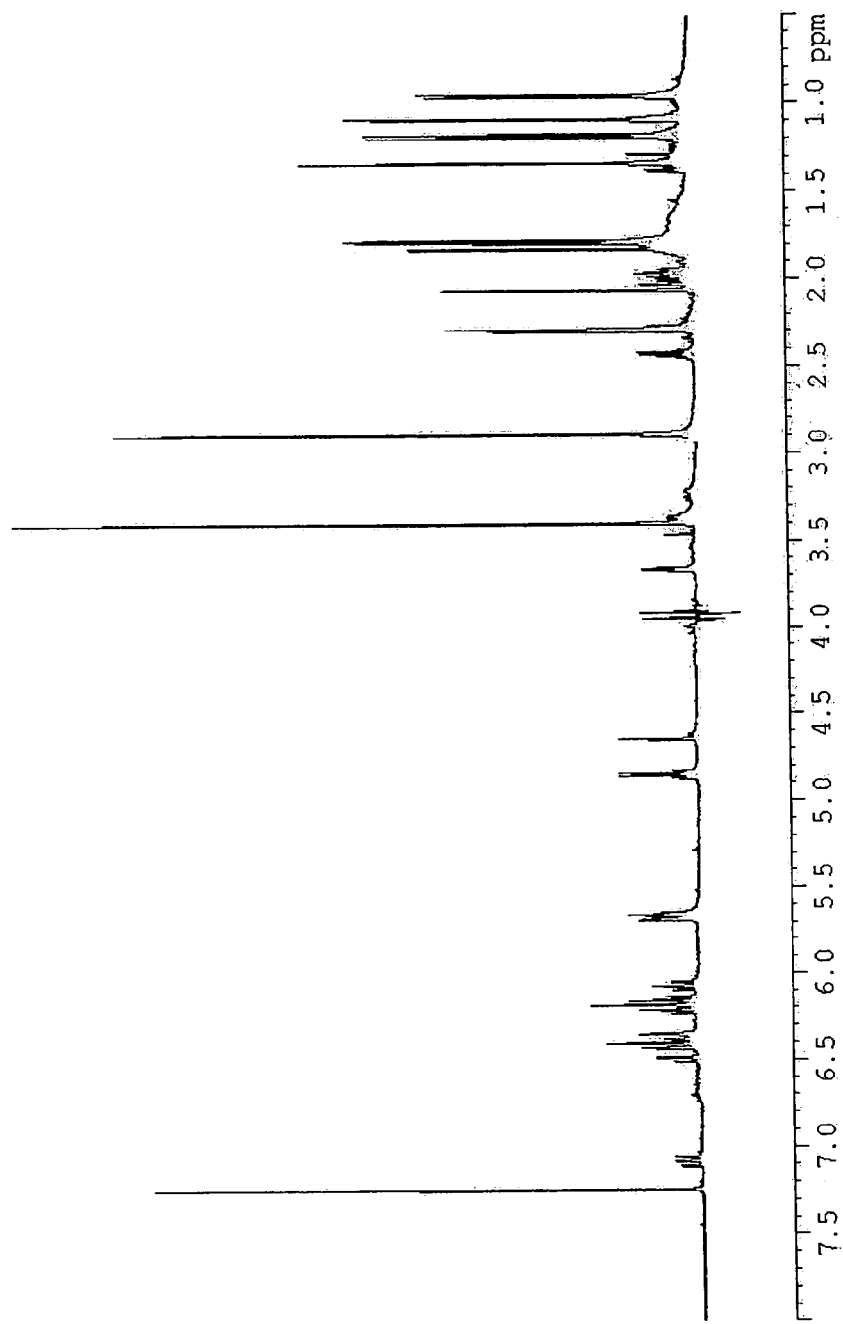
FIG. 11 shows the ID homonuculear decoupling spectrum of the compound of Formula (VI) in CDCl$_3$ irradiated at 3.96 ppm.

The geometry of the diene system was evaluated in a 1D homonuclear decoupling experiment by simultaneous irradiation of the H-7 and $H_2$-12 proton, which have similar resonance frequencies (FIG. 11). The residual H-8/H-9 and H-10/H-11 couplings were observed. The resulting multiplet comprised a doublet (J=14.3 Hz) and a doublet of doublets (J=14.7, 4.0 Hz), consistent with trans-trans geometry.

Figure 12:
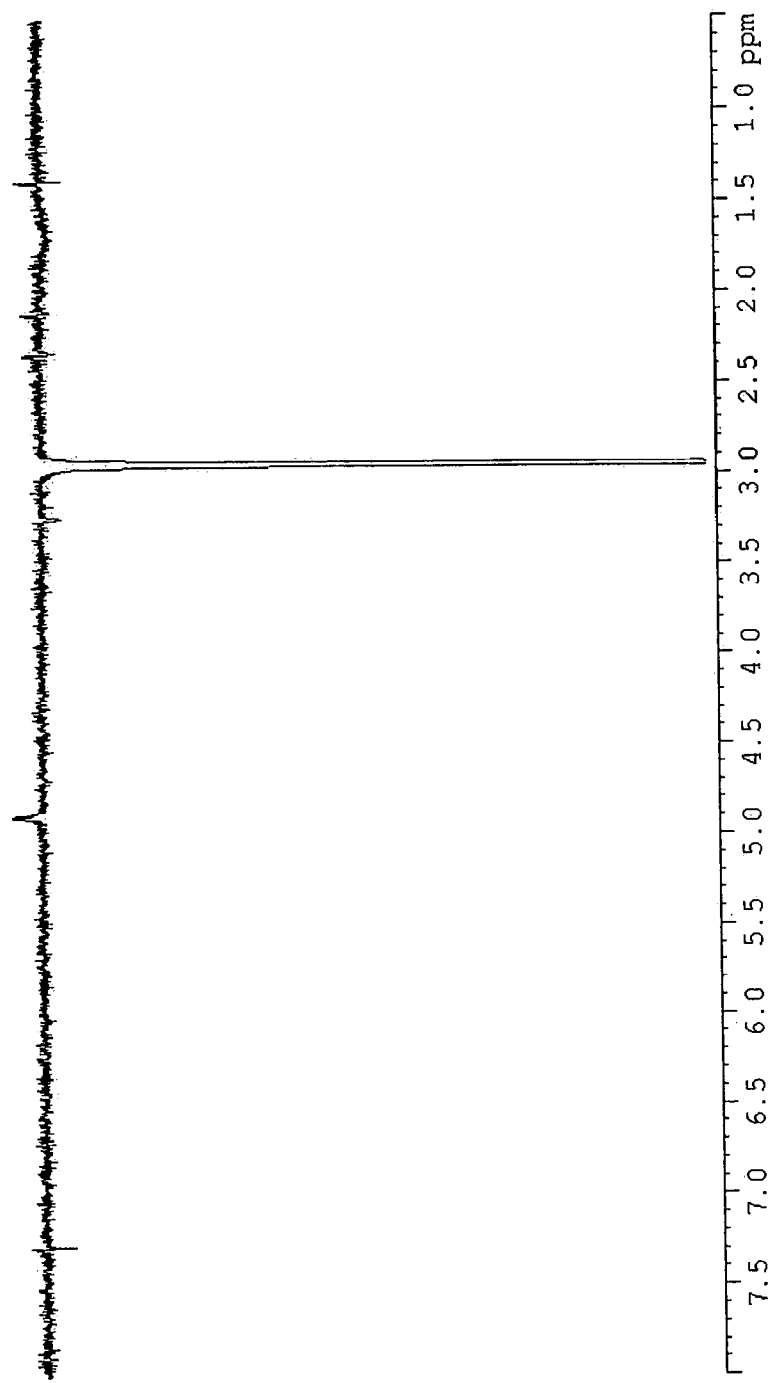
FIG. 12 shows the NOEDS spectrum of the compound of Formula (VI) in CDCl$_3$ irradiated at 2.94 ppm.

The stereochemistry of the spiro β-lactone-γ-lactam bicyclic ring system of oxazolomycin was originally reported based on X-ray crystallographic analysis of the p-bromobenzoate derivative of an ozonolysis product. (Mori, T.; Takahashi, K.; Kashiwabara, M.; Lemura, D.; Iwadare, S.; Shizuri, Y.; Mitomo, R.; Nakano, F.; Matsuzaki, A. Tetrahedron Lett. 1985, 26, 1073–1076; which is incorporated herein by reference in its entirety). The stereochemistry of the bicyclic ring system of 16-methyloxazolomycin was subsequently reported to be identical to that of oxazolomycin, and the additional chiral center at C-16 was assigned as S based on observation of an NOE between $H_3$-16-Me and N—Me. (Ryu, G.; Hwang, S.; Kim, S. J. Antibiotics 1997, 50, 1064–1066; which is incorporated herein by reference in its entirety). No such correlation was observed in the NOESY spectrum of the compound of Formula (VI); instead, the methine proton, H-16, was correlated to N—Me. This observation was confirmed through a ID NOEDS experiment, in which irradiation of N—Me resulted in enhancement of H-16 (see FIG. 12). Thus, the relative stereochemistry of the compound of Formula (VI) and 16-methyloxazolomycin appears to be different with respect to C-15 and C-16. In contrast, NOESY correlations between H-2 and H-4 suggest that the relative stereochemistry of C-2 and C-4 are the same in the compound of Formula (VI) and 16-methyloxazolomycin.

EXAMPLE 4

Anti-microbial Activity

Minimum inhibitory concentrations (MICs) were determined according to the National Committee for Clinical Laboratory Standards (NCCLS) susceptibility test guideline M7-A5 to quantify the anti-microbial activity of the compound of Formula (VI) against both gram-positive and gram-negative bacteria. Ferraro, M. 2001 Methods for Dilution Antimicrobial Susceptibility Tests for Bacteria that Grow Aerobically; Approved Standard (NCCLS), Villanova, which is incorporated herein by reference in its entirety. The serial micro broth dilution method used BBL Mueller-Hinton broth (cation adjusted) except for the Streptomyces pneumoniae which was tested in BBL Mueller-Hinton broth II (cation adjusted) with lysed horse blood. The final bacterial inoculum contained approximately $5 \times 10^5$ CFU/ml and was run on microtiter plates. The volume of each well was 100 μl and the plates were incubated at 35° C. for 18 hours. The MIC was defined as the lowest drug concentration that prevented visible growth of the bacterium. The results are reported in Table 2. The compound was active versus several microorganisms, especially gram-positive species.

TABLE 2

| MIC values for the compound of Formula (VI) against bacterial cell lines | |
|---|---|
| Organism | MIC (μg/ml) |
| Staphylococcus aureus - MSSA | 4 |
| Staphylococcus aureus - MRSA | 5 |
| Streptococcus pneumoniae - penicillin sensitive | 2 |
| Streptococcus pneumoniae - penicillin resistant | 1.5 |
| E. faecalis - Van$^s$ | 14 |
| E. faecium - Van$^r$ | 20 |
| E. coli - imp | 12 |

EXAMPLE 5

Growth Inhibition of Murine Melanoma, B16-F10 Cells

B16-F10 (ATCC; CRL-6475) a murine melanoma cell line was maintained in complete Dulbecco's Modification of Eagle's Medium (DMEM) (DMEM supplemented with 10% (v/v) Fetal bovine serum, 2 mM glutamine, 10 mM HEPES and Penicillin/Streptomycin at 100 IU/ml and 100 μg/ml respectively). The cells were cultured in an incubator at 37° C, 5% $CO_2$ and 95% humidified air.

For cell growth inhibition assays, B16-F10 cells were seeded at $1.25 \times 10^3$ cells/well in 90 μl complete media into Corning 3904 black-walled, clear-bottom tissue culture plates and the plates were incubated overnight to allow cells to establish and enter log phase growth. 20mM stock solutions of the compound of Formula (VI) were prepared in 100% DMSO. 10× concentrated serial dilutions of the compound of Formula (VI) were prepared in appropriate culture medium. Ten μl volumes of the 10× serial dilutions were added to the test wells in triplicate resulting in final concentrations ranging from 20 μM to 2 pM. The plates were returned to the incubator for 48 hours. The final concentration of DMSO was 0.25% in all samples.

Following 48 hours of drug exposure, 10 μl of 0.2 mg/ml Resazurin (obtained from Sigma-Aldrich Chemical Co.) in $Mg^{2+}$, $Ca^{2+}$ free phosphate buffered saline was added to each well and the plates were returned to the incubator for 3–6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an $EC_{50}$ value was not determined.

The data in Table 3 summarize the growth inhibitory effects of the compound of Formula (VI) against the murine melanoma, B16-F10 cell line.

TABLE 3

$EC_{50}$ value of the compound of Formula (VI) against B16–F10 cells

| | Formula (VI) Compound |
|---|---|
| $EC_{50}$ (μM) | 9.6 |

The $EC_{50}$ value indicates that the compound of Formula (VI) was able to inhibit the growth of B16-F10 tumor cells.

EXAMPLE 6

Pharmaceutical Formulations

1) Formulations Administered Intravenously by Drip, Injection, or the Like

Vials containing 5 g of powdered glucose are each added aseptically with 10 mg of a compound of Formulas (I)–(VI) and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor or as a method of treating bacterial infection in a human diagnosed as having such an infection. The solution is administered at between approximately 10 ml/day to approximately 1000 ml/day, intravenously, by drip, or via a subcutaneous or intraperitoneal injection, as deemed appropriate by those of ordinary skill in the art.

2) Formulation to Be Administered Orally or the Like

A mixture obtained by thoroughly blending 1 g of a compound of Formulas (I)–(VI), 98 g of lactose, and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors or bacterial infection in humans.

EXAMPLE 7

Anti-bacterial Administration

1) Infection with a Gram Positive Bacteria

An individual is diagnosed as suffering from a gram positive bacterial infection. An effective amount of a compound of Formulas (I), (II), or (III) or their acid-addition salts or pro-drug esters is administered to the individual and the bacterial infection is ameliorated.

2) Infection with *Staphylococcus aureus* (MSSA)

An individual is diagnosed as suffering from a *Staphylococcus aureus* (MSSA) infection. An effective amount of a compound of Formulas (I), (II), or (III) or their acid-addition salts or pro-drug esters is administered to the individual and the bacterial infection is ameliorated.

3) Infection with *Staphylococcus aureus* (MRSA)

An individual is diagnosed as suffering from a *Staphylococcus aureus* (MRSA) infection. An effective amount of a compound of Formulas (I), (II), or (III) or their acid-addition salts or pro-drug esters is administered to the individual and the bacterial infection is ameliorated.

4) Infection with *Staphylococcus pneumoniae*

An individual is diagnosed as suffering from a *Staphylococcus pneumoniae* infection. An effective amount of a compound of Formulas (I), (II), or (III) or their acid-addition salts or pro-drug esters is administered to the individual and the bacterial infection is ameliorated.

5) Infection with *Enterococcus faecalis* (VSE)

An individual is diagnosed as suffering from a *Enterococcus faecalis* (VSE) infection. An effective amount of a compound of Formulas (I), (II), or (III) or their acid-addition salts or pro-drug esters is administered to the individual and the bacterial infection is ameliorated.

6) Infection with *Enterococcus faecium* (VRE)

An individual is diagnosed as suffering from a *Enterococcus faecalis* (VRE) infection. An effective amount of a compound of Formulas (I), (II), or (III) or their acid-addition salts or pro-drug esters is administered to the individual and the bacterial infection is ameliorated.

7) Infection with *Escherishia coli*

An individual is diagnosed as suffering from a *Escherishia coli* infection. An effective amount of a compound of Formulas (I), (II), or (III) or their acid-addition salts or pro-drug esters is administered to the individual and the bacterial infection is ameliorated.

EXAMPLE 8

Anti-cancer Administration

An individual is diagnosed as suffering from melanoma. An effective amount of a compound of Formulas (I), (II), or (III) or their acid-addition salts or pro-drug esters is administered to the individual and the melanoma is ameliorated.

The examples described above are set forth solely to assist in the understanding of the invention. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed is:

1. A compound having the structure of Formula (I) and acid-addition salts and pro-drug esters thereof:

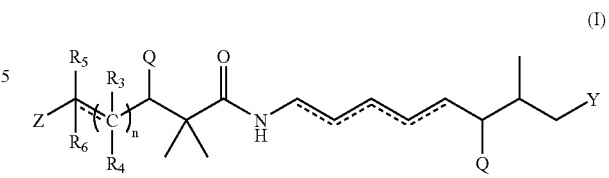

wherein $R_3$, $R_4$, $R_5$, and $R_6$ are each separately selected from the group consisting of hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy, or are separately absent when necessary to accommodate double bonds;

Y has the following structure:

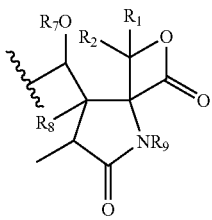

$R_1$, $R_2$, and $R_8$ are each separately selected from the group consisting of a hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy;

$R_7$ and $R_9$ are each separately selected from the group consisting of hydrogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, and cycloalkenyl;

Q is an optionally substituted O or S;

Z is $NO_2$;

n is an integer from 0 to 10;

any bond represented by a dashed and solid line represents a bond selected from the group consisting of a carbon-carbon single bond and a carbon-carbon double bond;

when n is greater than 1, each unit n is bonded to any adjacent units n via carbon-carbon single bonds or carbon-carbon double bonds; and any carbon-carbon double bond has a configuration selected from the group consisting of cis and trans.

2. The compound of claim 1 wherein Q is selected from the group consisting of OH and SH.

3. The compound of claim 1 wherein $R_3$, $R_4$, $R_5$, and $R_6$ are each separately selected from the group consisting of H and $CH_3$ or are separately absent when necessary to accommodated double bonds.

4. The compound of claim 1 wherein n is 7.

5. The compound of claim 4 having the structure of Formula (IV):

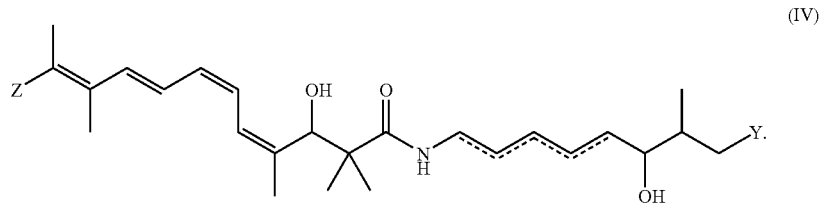

6. The compound of claim 5 wherein Y has the structure:

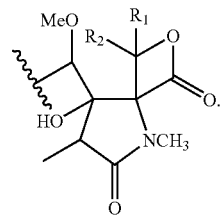

7. The compound of claim 6 wherein $R_1$ is H and $R_2$ is $CH_3$.

8. The compound of claim 7 having the structure of Formula (VI):

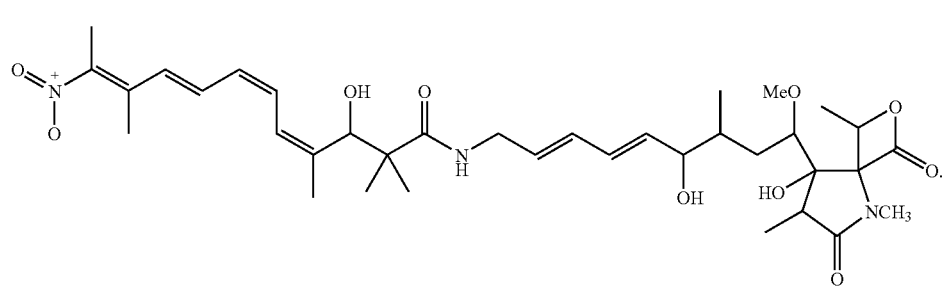

9. A compound having the structure of Formula (II) and acid-addition salts and pro-drug esters thereof:

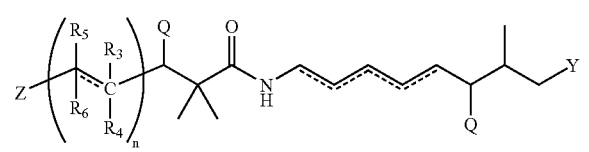

wherein $R_3$, $R_4$, $R_5$, and $R_6$ are each each separately selected from the group consisting of hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy, or are separately absent when necessary to accommodate double bonds;

Y has the following structure:

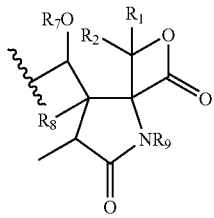

$R_1$, $R_2$, and $R_8$ can be each separately selected from the group consisting of a hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy;

$R_7$ and $R_9$ are each separately selected from the group consisting of hydrogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, and cycloalkenyl;

Q is an optionally substituted O or S;

Z is $NO_2$;

n is an integer from 0 to 10;

any bond represented by a dashed and solid line represents a bond selected from the group consisting of a carbon-carbon single bond and a carbon-carbon double bond; and any carbon-carbon double bond has a configuration selected from the group consisting of cis and trans.

10. The compound of claim 9 wherein Q is selected from the group consisting of OH and SH.

11. The compound of claim 9 wherein $R_3$, $R_4$, $R_5$, and $R_6$ are each separately selected from the group consisting of H and $CH_3$ or are separately absent when necessary to accommodated double bonds.

12. The compound of claim 9 having the structure of Formula (IIb):

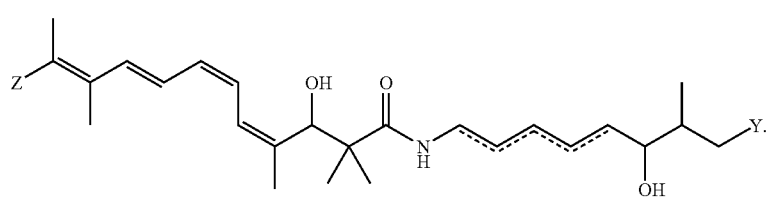

(IIb)

wherein the configuration of each unit n in the compound of Formula (IIb) is separately selected from cis and trans.

13. The compound of claim 9 wherein n is 4.

14. The compound of claim 13 having the structure of Formula (IV):

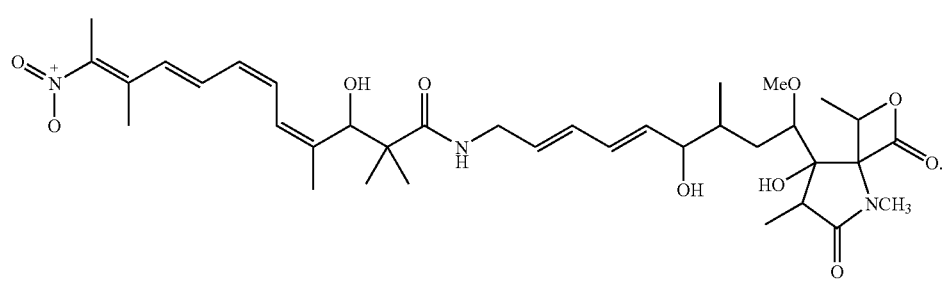

(IV)

15. The compound of claim 14 wherein Y has the structure:

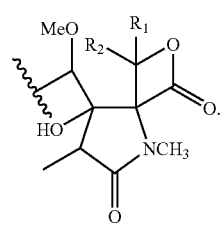

16. The compound of claim 15 wherein $R_1$ is H and $R_2$ is $CH_3$.

17. The compound of claim 16 having the structure of Formula (VI):

18. A compound having the structure of Formula (III) and acid-addition salts and pro-drug esters thereof:

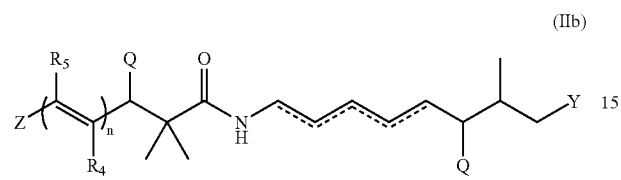

(III)

wherein $R_3$, $R_4$, $R_{13}$, and $R_{14}$ are each separately selected from the group consisting of hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy, or are separately absent when necessary to accommodate double bonds;

$R_5$ and $R_6$ are each separately selected from the group consisting of hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, and cycloalkenyl, or may each be separately absent when necessary to accommodate double bonds;

Y has the following structure:

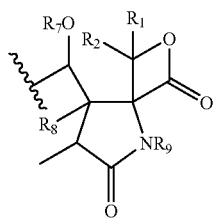

$R_1$, $R_2$, and $R_8$ can be each separately selected from the group consisting of a hydrogen atom, halogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, cycloalkenyl, and hydroxy;

(VI)

R<sub>7</sub> and R<sub>9</sub> are each separately selected from the group consisting of hydrogen atom, mono-substituted, poly-substituted or unsubstituted variants of the following residues: saturated $C_1$–$C_{10}$ alkyl, unsaturated $C_2$–$C_{10}$ alkenyl or $C_2$–$C_{10}$ alkynyl, cycloalkyl, and cycloalkenyl;

n is an integer from 0 to 6;

Q is an optionally substituted O or S;

Z is $NO_2$;

any bond represented by a dashed and solid line represents a bond selected from the group consisting of a carbon-carbon single bond and a carbon-carbon double bond;

when n is greater than 1, each unit n is bonded to any adjacent units n via carbon-carbon single bonds or carbon-carbon double bonds; and any carbon-carbon double bond has a configuration selected from the group consisting of cis and trans.

19. The compound of claim 17 wherein Q is selected from the group consisting of OH and SH.

20. The compound of claim 18 wherein $R_3$, $R_4$, $R_{13}$, and $R_{14}$ are each separately selected from the group consisting of H and $CH_3$ or are separately absent when necessary to accommodated double bonds and $R_5$ and $R_6$ are each separately selected from the group consisting of H and $CH_3$, or are separately absent when necessary to accommodate double bonds.

21. The compound of claim 18 wherein n is 6.

22. The compound of claim 21 having the structure of Formula (IV):

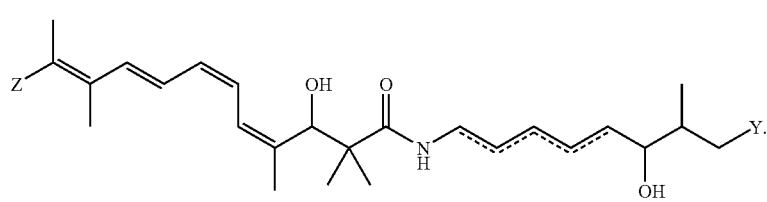

(IV)

23. The compound of claim 22 wherein Z is $NO_2$ and Y has the structure:

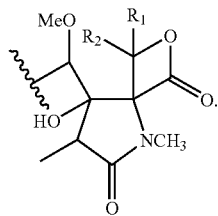

24. The compound of claim 23 wherein $R_1$ is H and $R_2$ is $CH_3$.

25. The compound of claim 24 having the structure of formula (VI):

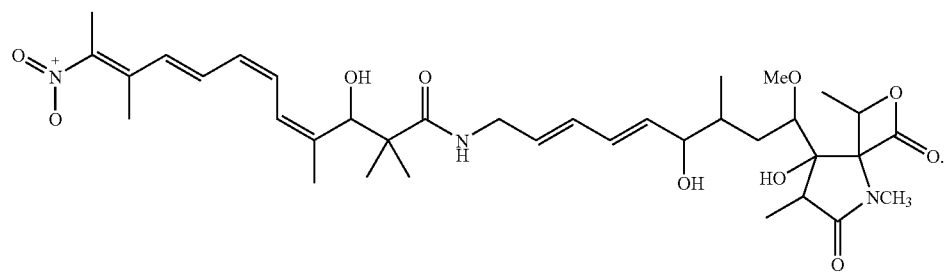

(VI)

26. A method of treating an individual infected with a bacteria, comprising: administering to the individual a compound selected from the group consisting of the compounds of claims 1, 9, or 18, their acid-addition salts, and pro-drug esters.

27. The method of claim 26 wherein the bacteria is a gram positive bacteria.

28. The method of claim 27 wherein the bacteria is *Staphylococcus aureus* (MSSA).

29. The method of claim 27 wherein the bacteria is *Staphylococcus aureus* (MRSA).

30. The method of claim 27 wherein the bacteria is *Streptococcus pneumoniae*.

31. The method of claim 27 wherein the bacteria is *Enterococcus faecalis* (VSE).

32. The method of claim 27 wherein the bacteria is *Enterococcus faecium* (VRE).

33. The method of claim 26 wherein the bacteria is *Escherichia coli*.

34. A method of treating an individual with melanoma, comprising: administering to the individual a compound selected from the group consisting of the compounds of claims 1, 9, or 18, their acid-addition salts, and pro-drug esters.

35. A method of treating melanoma comprising the step of contacting a cancer cell with a compound selected from the group consisting of the compounds of claims 1, 9, or 18, their acid-addition salts, and pro-drug esters.

36. A method of treating melanoma comprising contacting a patient diagnosed with cancer with a compound selected from the group consisting of the compounds of claims 1, 9, or 18, their acid-addition salts, and pro-drug esters.

* * * * *